United States Patent
St Amant, III

(10) Patent No.: US 10,073,013 B2
(45) Date of Patent: Sep. 11, 2018

(54) MODULAR SAMPLE SYSTEM INCORPORATING MOUNTING BRACKET INDEPENDENT OF HOUSING, AND METHOD THEREFORE

(71) Applicant: Mayeaux Holding LLC, Gonzales, LA (US)

(72) Inventor: Valmond Joseph St Amant, III, St Amant, LA (US)

(73) Assignee: Mayeaux Holding, LLC, Gonzales, LA (US)

( * ) Notice: Subject to any disclaimer, the term of this patent is extended or adjusted under 35 U.S.C. 154(b) by 16 days.

(21) Appl. No.: 15/228,814

(22) Filed: Aug. 4, 2016

(65) Prior Publication Data

US 2017/0234777 A1    Aug. 17, 2017

Related U.S. Application Data

(60) Provisional application No. 62/202,478, filed on Aug. 7, 2015.

(51) Int. Cl.
*G01N 1/14* (2006.01)
*G01N 1/20* (2006.01)
(Continued)

(52) U.S. Cl.
CPC ......... *G01N 1/2035* (2013.01); *G01N 1/2247* (2013.01); *G01N 1/44* (2013.01); *G01N 2001/205* (2013.01)

(58) Field of Classification Search
CPC .............. G01N 1/2214; G01N 30/20; G01N 2001/2267; G01N 1/2247; G01N 30/30;
(Continued)

(56) References Cited

U.S. PATENT DOCUMENTS 5,109,709 A * 5/1992 Nimberger ............... G01N 1/14
 73/863.84
5,531,130 A   7/1996 Welker
(Continued)

OTHER PUBLICATIONS

Mustang Sampling LLC, Mustang Intelligent Vaporizer Sampling System Model 2/MIV2, Product Sheet, (C) 2009-2016, vol. 2.6, Mustang Sampling LLC, US.
(Continued)

*Primary Examiner* — Harshad R Patel
*Assistant Examiner* — Brandi Hopkins
(74) *Attorney, Agent, or Firm* — Joseph T Regard Ltd plc

(57) ABSTRACT

A modular sample conditioning system formed for in-situ sampling installation, referenced herein as "source mounted". The present invention relates to a docking platform or substrate configured to receive multiple, diverse sampling components in various flow configurations, coupled with a unique housing/enclosure formed to engage the docking platform so as to further strengthen and stabilize the mount, the enclosure also formed to engage one or more of the mounted sampling components, so as to provide access outside of the enclosure for visibility and/or manual access of same, providing an easily installed and maintained, user-accessible, on-site modular sampling conditioning/monitoring system.

28 Claims, 26 Drawing Sheets

(51) Int. Cl.
*G01N 1/22* (2006.01)
*G01N 1/44* (2006.01)

(58) Field of Classification Search
CPC ............... G01N 1/2258; G01N 1/2252; G01N 2001/2282; G01N 2001/2261; G01N 2001/244; G01N 2001/2238; G01N 2001/105; G01N 21/3577; G01N 21/431; G01N 2021/432; G01N 33/225; G01N 2021/434; G01D 11/30
See application file for complete search history.

(56) References Cited

U.S. PATENT DOCUMENTS

| | | | | |
|---|---|---|---|---|
| 6,092,519 | A | * | 7/2000 | Fish ..................... F17C 13/00 126/263.01 |
| 6,357,304 | B1 | * | 3/2002 | Mayeaux ............. G01N 1/2035 73/863.12 |
| 6,701,794 | B2 | | 3/2004 | Mayeaux |
| 6,904,816 | B2 | | 6/2005 | Mayeaux |
| 7,004,041 | B2 | | 2/2006 | Mayeaux |
| 7,134,318 | B2 | | 11/2006 | Mayeaux |
| 7,162,933 | B2 | | 1/2007 | Thompson et al. |
| 8,196,480 | B1 | | 6/2012 | Mayeaux |
| D674,052 | S | | 1/2013 | Thompson |
| 2012/0325694 | A1 | * | 12/2012 | Thompson ............. B65D 81/38 206/216 |

OTHER PUBLICATIONS

Mustang Sampling LLC, Mustang Sample Conditioning System/MSCS, Product Sheet, (C) 2009-2016, vol. 1.4, Mustang Sampling LLC, US.
Mustang Sampling LLC, Mustang Sample Conditioning System /P53, Product Sheet, (C) 2009-2016, vol. 2.1, Mustang Sampling LLC, US.
Mustang Sampling, LLC, Mustang Pony Heated Probe Enclosure, Product Sheet, (C) 2009-2016, vol. 4.3, Mustang Sampling LLC, US.
Welker Inc, SCHS Sample Conditioning Heated System, Product Sheet, (C) 2016, vol. 05-16/200, Welker Inc, US.
Intertec-Hess GMBH, Intertec Product Enclosures, web page, www.intertec.info/v2/index.php/en/enclosures. (C) 2014, Intertect-Hess GMBH, Germany.
Emerson Electric Co, Drawing 370XA Multi-Stream Enclosure 72904, www.emerson.com/documents/automation/drawing-370xa-multi-stream-enclosure-en-72904.pdf, Ver 3 Jan. 7, 2016, US.
Emerson Electric Co, Drawing 370XA Multi-Stream Enclosure 72902, www.emerson.com/documents/automation/drawing-370xa-multi-stream-enclosure-en-72902.pdf, Ver 3 Jan. 7, 2016, US.
Spectrasensors Inc, SS500/SS2000/SS3000 Gas Analyzer Installation/Maintenance Manual, (C) 2016, See pp. A-9, A-10, PN 4900002215 Rev D, SpectraSensors Inc, US.
Intertec-Hess GMBY, Intertec Multibox 170, Product Sheet, downloaded Feb. 5, 2018 from /www.intertec.info/documents/en/kd128en.pdf, KD128010en, US.

* cited by examiner

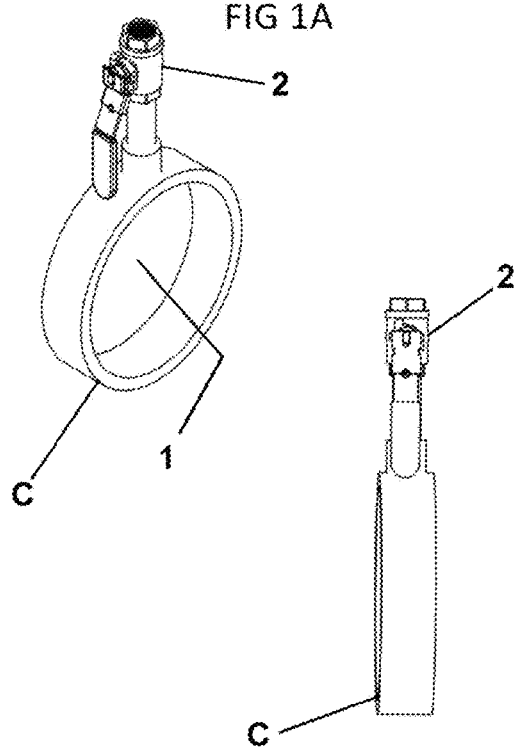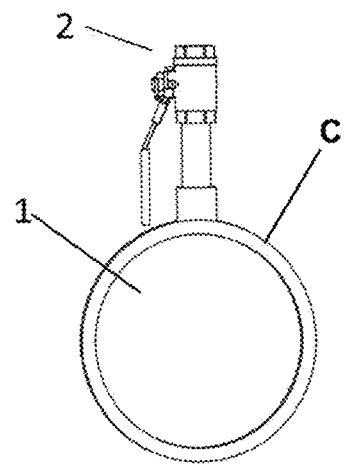

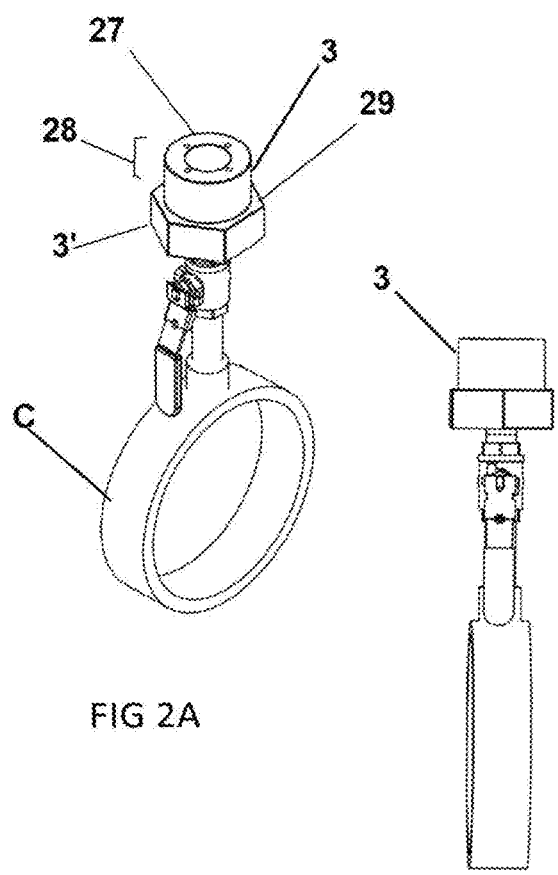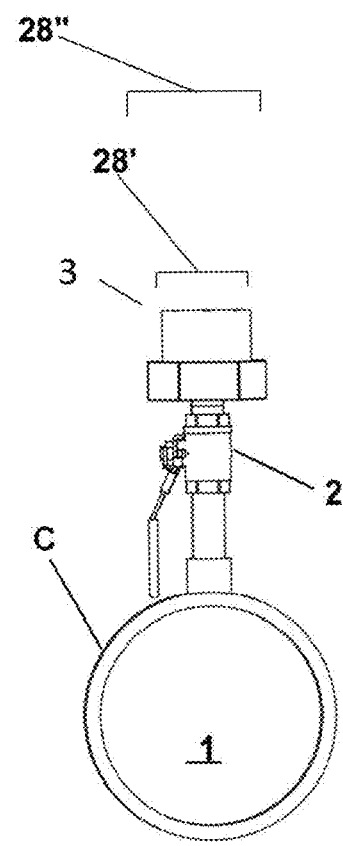
FIG 2A  FIG 2B  FIG 2C

5

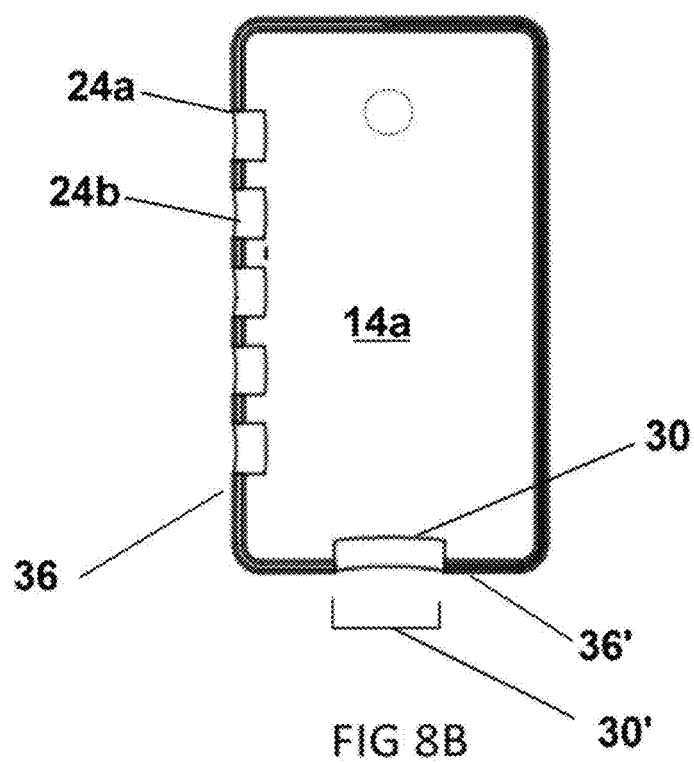

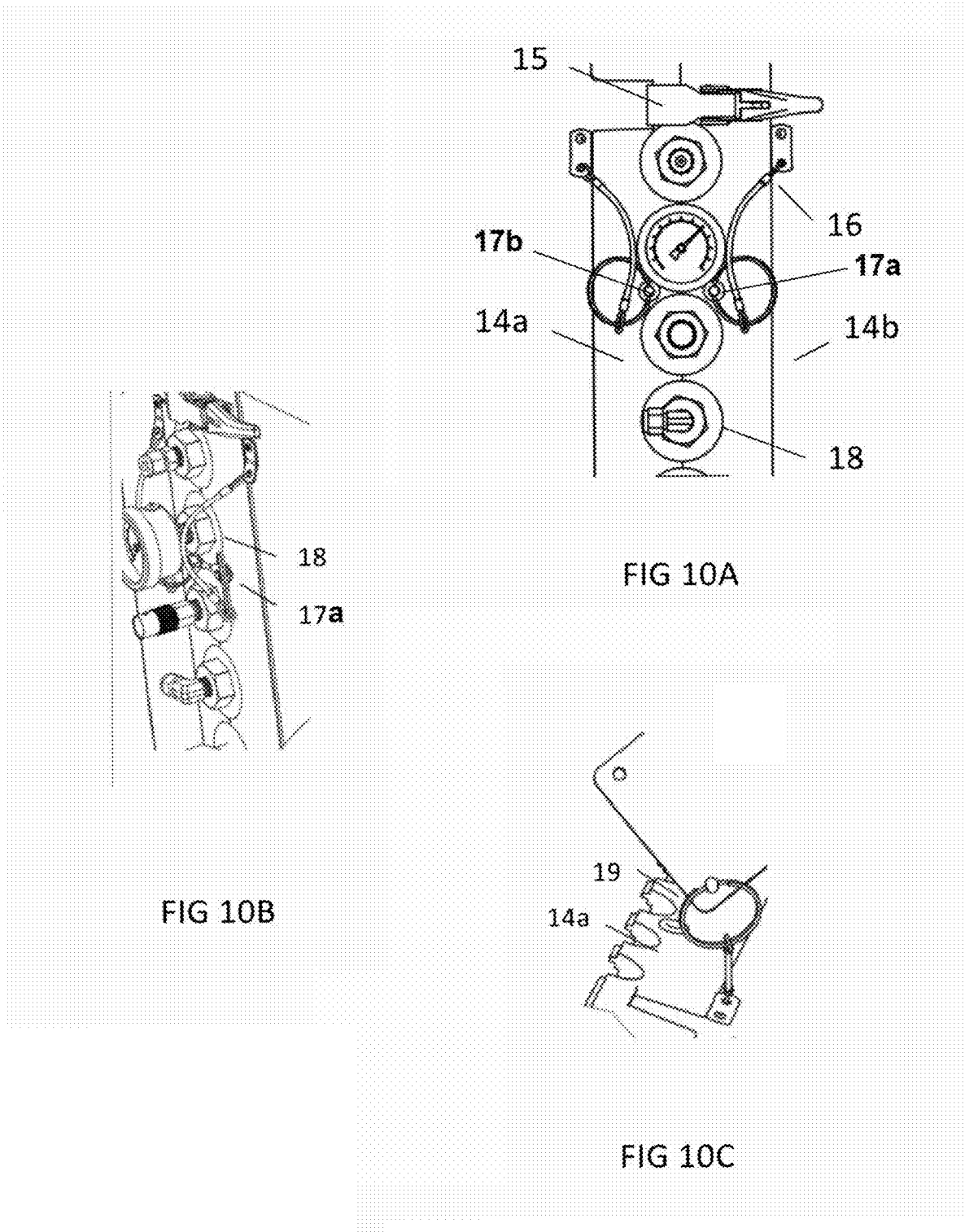

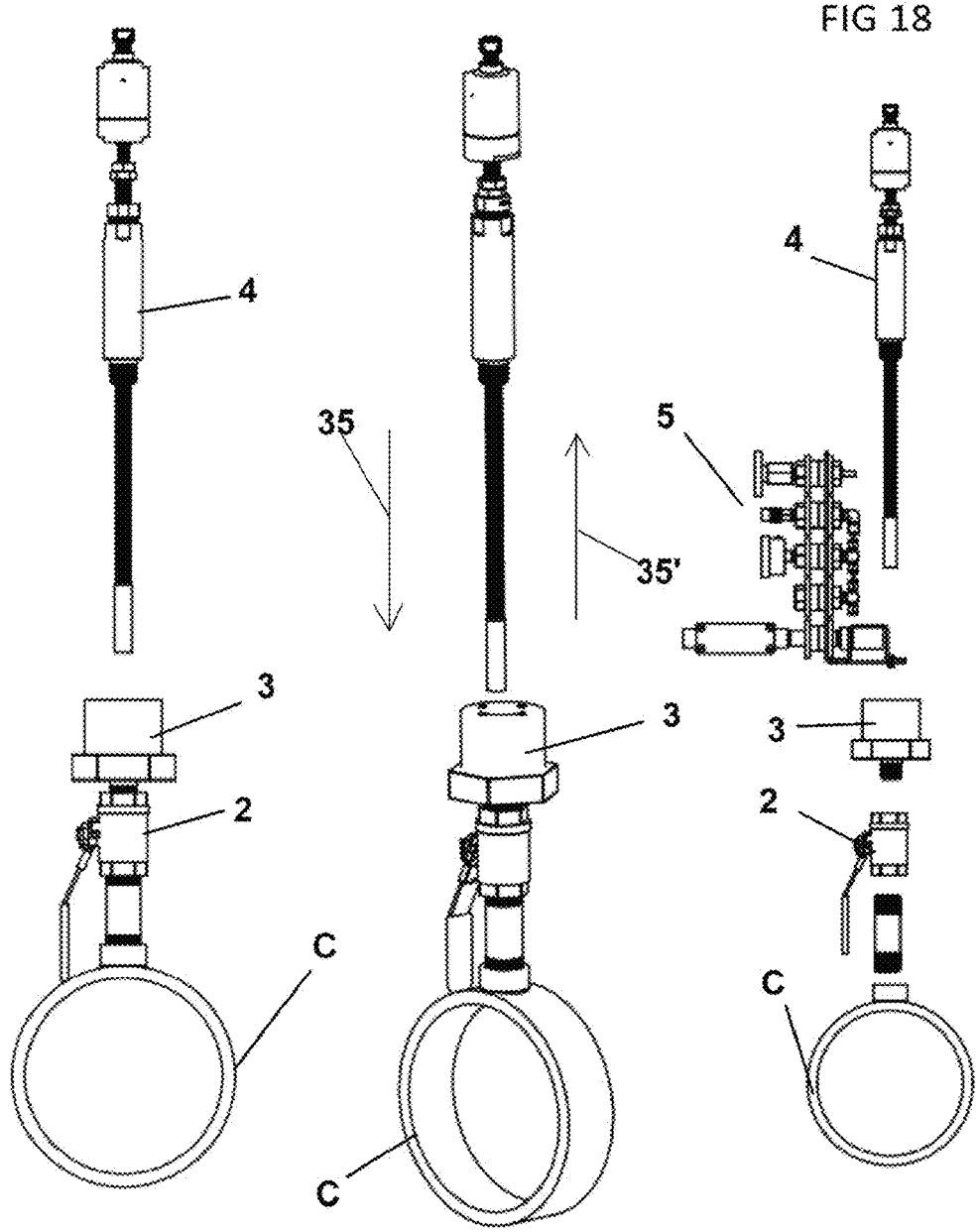

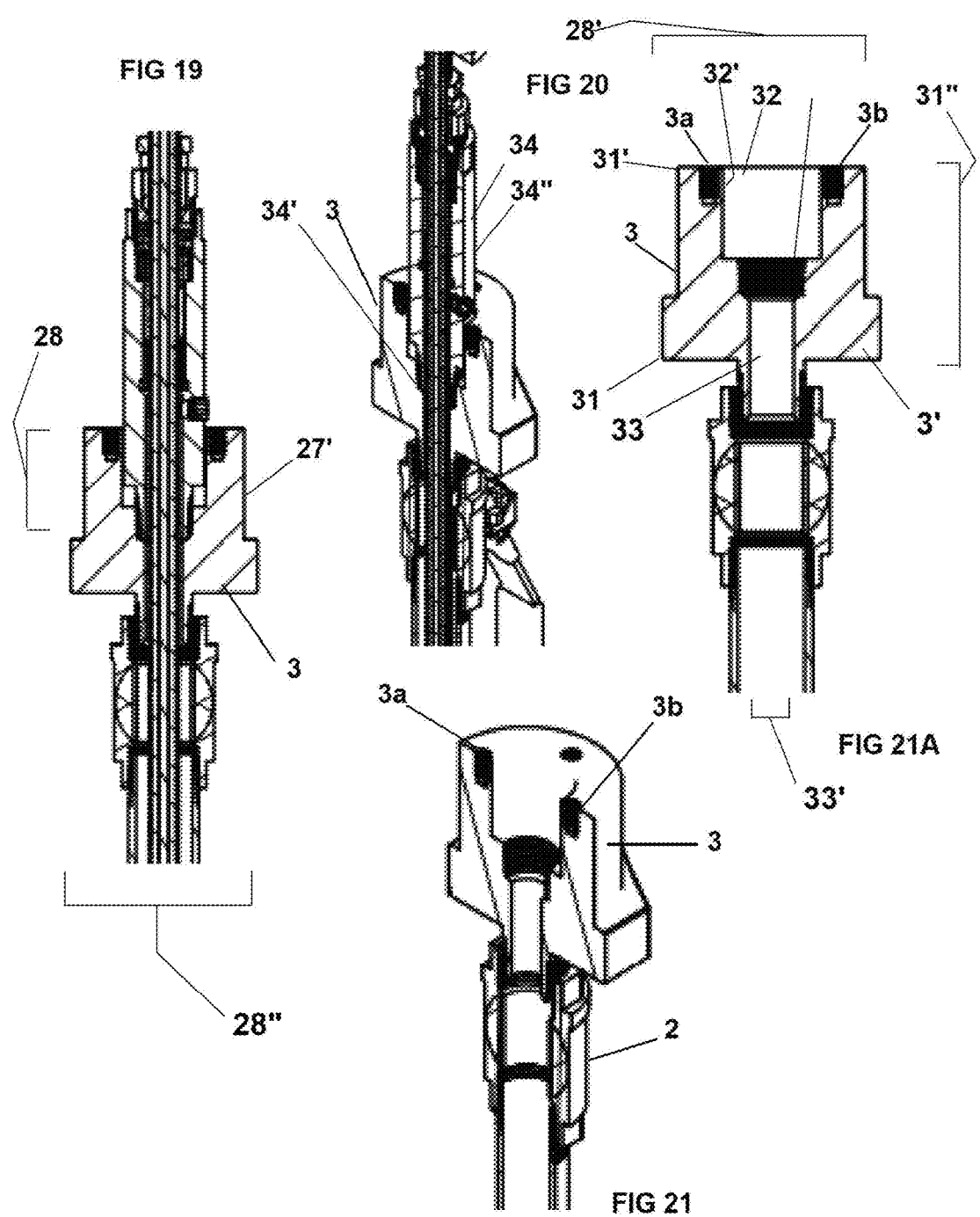

MODULAR SAMPLE SYSTEM INCORPORATING MOUNTING BRACKET INDEPENDENT OF HOUSING, AND METHOD THEREFORE

BENEFIT CLAIM

The present application claims the benefit of U.S. Provisional Patent Application Ser. No. 62/202,478 filed Aug. 7, 2015, entitled "Source Mounted Modular Sample Conditioning System", listing Valmond Joseph St Amant, III as inventor.

FIELD OF THE INVENTION

This invention relates to sampling of pressurized process fluids for on-streaming, as well as spot sampling of pressurized process fluids such as natural gas or the like having liquid entrained therein, otherwise referenced as multiphase or "wet". The preferred embodiment of the present invention contemplates a modular sample conditioning system provided for an in-situ sampling installation, referenced herein as "source mounted". The preferred embodiment of the present invention also relates to a docking platform or substrate configured to receive multiple, diverse sampling components customizable to various flow configurations, coupled with a unique housing/enclosure formed to engage the docking platform so as to further strengthen and stabilize the mount, the enclosure also formed to engage one or more of the mounted sampling components, so as to provide access exterior the enclosure for enhanced visibility and/or manual access of same, providing an easily installed and maintained, user-accessible, on-site modular sampling conditioning/monitoring system.

BACKGROUND OF THE INVENTION

Natural gas is bought and sold based on its heating value. It is the BTU content that determines the monetary value of a given volume of natural gas. This BTU value is generally expressed in decatherms (one million BTU). In the determination of total heat value of a given volume of gas, a sample of the gas is analyzed and from the composition its heat value per unit volume is calculated. This value is generally expressed in BTU/cu ft. The typical range of transmission quality gas ranges between 1000 and 1100 BTU/cu ft. Production gas, storage facility gas, NGL, and new found Shale Gas can have much higher heating values up to or even exceeding 1500 BTU/cu ft.

There has been a long standing controversy between gas producers and gas transporters regarding entrained liquid typically present in most high BTU/cu ft gas (rich or "wet" gas). Transporter tariffs require essentially liquid-free gas, while hydrocarbon liquid in the gas being transported causes operational and safety problems. Accordingly, the practice is to separate the liquid before entering a transport (pipe) line.

The API 14.1 standards (Manual of Petroleum Measurement Standards, 2006) scope does not include supercritical fluid (dense phase) or "wet gas" "(a term referenced by the Natural Gas industry as a gas that is at or below its hydrocarbon dew point temperature and/or contains entrained liquid), nor does the GPA 2166 standard (Obtaining Natural Gas Samples for Analysis by Gas Chromatography, 2005). In short, there is no presently known standard which defines how to obtain a "representative sample" of a natural gas supply having entrained hydrocarbon in any form.

Accordingly, to fully comply with the current industry standards, entrained liquids must be removed when using sample systems. Membrane-tipped probes such as the A+ Corporation Genie Probe (see U.S. Pat. No. 357,304, U.S. Pat. No. 6,701,794, U.S. Pat. No. 6,904,816, U.S. Pat. No. 7,004,041, and U.S. Pat. No. 7,134,318) have been used for many years to shed entrained liquids inside pressurized pipelines to obtain samples or the like. Other companies such as Valtronics, Inc/Mustang Sampling have bolted enclosures to the A+ Corporation membrane-tipped probes, then placing A+ Corporation Genie membrane separators in a second enclosure mounted closer to the analyzer. See, for example, Mayeaux U.S. Pat. No. 6,357,304, Thompson U.S. Pat. No. 7,162,933, Thompson US 2012/0325694 A1 (FIG. 1), as well as Thompson D674,052. Other companies, such as Welker Engineering, use non-membrane probes (fixed "stinger" probes) and bring the liquids outside the pipeline to reject them outside the pipeline, hanging a hinged enclosure onto the probe (see Welker SCHS brochure). Welker and other companies such as PGI install sample pumps and composite samplers and bolt enclosures to the pipeline (see Welker U.S. Pat. No. 5,531,130 and Nimberger U.S. Pat. No. 5,109,709).

Each of these enclosure systems are engineered for one specific configuration, and once the probe housing or pump is installed, it cannot be removed without shutting down and depressurizing the process.

In Thompson U.S. Pat. No. 7,162,933, we see an enclosure which has been believed utilized with a Mayeaux U.S. Pat. No. 6,357,304 probe. The enclosure has mating upper and lower horizontal halves. Welker U.S. Pat. No. 5,531,130 has a similar two half-horizontal approach.

The Welker SCHS brochure depicts a vertical version of the two, half enclosure with a hinged door design. Nimberger U.S. Pat. No. 5,109,709 utilizes a hinged door as well. Thompson US 2012/0325694 A1 attempts to increase access to the probe inside the enclosure by using a diagonal-half approach. While this change may increase accessibility by 20%-30%, it still leaves much to be desired for component access. Further, the pipeline must be shut down and depressurized to install and remove the probe with all the prior art.

GENERAL SUMMARY DISCUSSION OF THE INVENTION

The present invention provides a unique system designed to solve the prior art problems relating to access, ease of use, and flexibility as it relates to source mounted sample systems.

More specifically, unlike prior art, the present invention is modular. It is uniquely designed with a common substrate to accommodate various diverse and different configurations. This modular approach allows common inventory that facilitates lean manufacturing techniques.

The system substrate has a common source coupling that facilitates a common bracket which utilizes a common enclosure with a common array of pre-drilled holes. This modular platform substrate allows components or modules to be put in different flow path order, deleted or added, or changed without affecting the probe or the size of the enclosure and all using the same base substrate. The probe or pump is independent of the modular sample system.

Another benefit of this invention is the fact that a spare module may be kept in stock and replaced in the field. So should extensive maintenance be necessary, the entire sample system module could be replaced (without shutting down the process and without removing the probe) by a less skilled technician, and then the troubled system could be returned to a central facility where more experienced technicians can trouble shoot and repair it or just clean if it necessary.

Further, unlike prior art, the present invention facilitates 100% access to all components. It accomplishes this objective without the need for hinges or diagonal cuts. The system is designed so that the enclosure is independent of the probe or pump and the components. The enclosure can be easily and completely removed without disturbing the probe or any other components of the system. The modular system is independent of the probe and the enclosure.

Finally, although the present invention is modular and an assemblage of several components, namely the base, mounting bracket, modular sample components, and enclosure components, the present system is configured so that the assemblage is structurally integrated to increase rigidity in the overall structure, providing a stable docking platform able to receive a diverse selection of components such as electronic, electrical, flow control, sample conditioning, monitoring, etc, while allowing the components to be easily mounted in customized fashion with environmental protection, but exterior visibility and control access as desired.

Components typically used in analyzer sample conditioning that technicians need visibility may comprise the pressure gauge, temperature gauge, outlet fitting, relief valve, conduit wiring connection, and others. The technician needs to be able to read (visually access) the pressure and temperature gauges, and physically access the outlet fitting, and inspect the conduit wiring, as well as inspect the relief valve to verify that it is not activated. Other components such as tubing and fittings and valves only need to be infrequently accessed for service or maintenance, and therefore not be visible exterior the housing, while the previously listed components need to be visible by the technician. The present invention allows the visibility of those components without having to open or disassemble the enclosure (housing).

In addition, the housing/enclosure of the present system provides protection from the environment with the aforementioned exterior access/visibility of desired components, as well as all components AND tubing when the enclosure is removed. All the while, the system maintains its system rigidity, and access to the interior of the housing requires no breaking of fittings or connection or disassembly of the system.

The housing formed in the present invention can include environmental isolation wherein the housing is insulated so as to allow the selective changing of temperature therein, and can be heated and even powered from an existing heat trace tubing bundle coming from an analyzer.

Unlike the prior art, the present system, being completely modular, allows a technician to remove the entire sample system and replace it with a spare while using the same enclosure and substrate coupling. In such a retrofit, the substrate coupling need not be removed from the process isolation valve. Further, the probe need not be removed from the process pipe, because the probe is also independent of the base substrate and the enclosure, as designed.

The preferred embodiment of the present invention (FIGS. 1-11B) teaches a system wherein the modular sample system is mounted at the source of the sample (in situ).

A second embodiment would be (FIGS. 12A-12B) contemplates the modular sample system situated downstream of the source, but before an analyzer.

A third embodiment discloses the modular sample system 5 at the analyzer A, or configured into the analyzer. (FIG. 13)

Other embodiments could include portable sample conditioning systems situated upstream the analyzer A' (FIGS. 14-15).

In summary, the present invention contemplates a unique, customizable modular sample system formed to receive a diverse selection of components such as electronic, electrical, flow control, etc, each mounted to a non-customized substrate and enclosure (housing). The mount of the present system is configured for easy mounting of a diverse array of components into a customizable configuration, while providing effective protection from the environment with exterior visibility and control of certain components.

Finally, the system as configured provides an enclosure which is easily disassembled, providing 100% access to all components when the enclosure is removed, while maintaining the rigidity of the system, and without the necessity of having to break any fittings or connection, or interfere with the operation of any extraction device present, or otherwise require the disassembly of the flow system for general maintenance/inspection.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIGS. 1A-1C are partially cut-away, isometric, side, and end views, respectively, of a pressurized source contained in a pipeline or conduit C, with an isolation valve mounted thereto.

FIGS. 2A-2C are isometric, side, and end views of the device of FIGS. 1A-1C, respectively, showing isolation valve 2 with the substrate coupling 3 mounted thereto.

FIG. 4A-4B shows opposing perspective views of various components (alternatively referenced as modular components or modular sample components) forming a modular sample conditioning system 5, the components mounted to the substrate bracket or, alternatively referenced, mounting bracket; some of the components in the illustrated embodiment are configured to receive sample fluid flow therethrough for treatment (such as pressure regulator or heater), or providing a visual readout on indication (such as a gauge), or control (such as a valve) or support (such as an electrical connection), or the like.

FIG. 8B is an end view of the housing/enclosure of FIG. 8A, illustrating the configuration of the unit including the holes or apertures formed therethrough for external access to modular components (along the side wall edge of housing enclosure 20) as well as a mounting aperture mounting the housing situated at the bottom or end of the unit (in the preferred embodiment of the present invention).

FIGS. 10A-10C are frontal, close-up and perspective views of the housing for the modular sample conditioning components of FIGS. 9A-9C, with user viewable and control components accessible via openings in said housing/enclosure, as well as pins 17 used for alignment of the enclosure components with gaskets 18 therebetween and held in place via clasps 15, as well as retaining of the enclosure component(s) when same is opened for access.

FIG. 16 is an end, partially exploded view of the invention of FIGS. 3A-3C.

FIG. 17 is a perspective, partially exploded view of the invention of FIG. 16

FIG. 18 is an end, exploded view of the invention of FIGS. 7A-7C.

FIG. 19 is a side, partial, cut-away view of the system of FIGS. 3A-3C.

FIG. 20 is a side, perspective close-up, cut-away view, of the invention of FIG. 3A.

FIG. 21 is an isometric, cut-away, close-up, view of the substrate coupling mounted to the isolation valve.

FIG. 21A is a cross-sectional view of the device of FIG. 21.

DETAILED DISCUSSION OF THE INVENTION

Figure 3A:
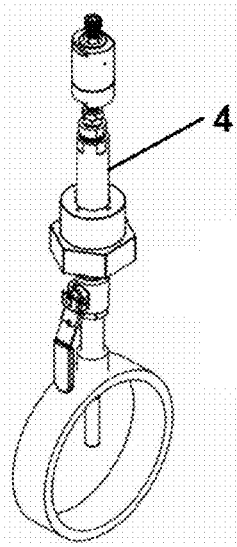
FIGS. 3A-3C are isometric, side, and end views of the device of FIGS. 2A-2C, respectively, with an exemplary extraction device 4 in the form of an insertion probe mounted to the substrate coupling.
Figure 3B:
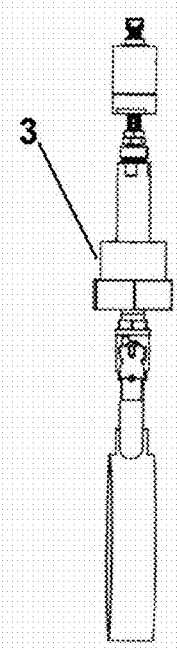
Figure 3C:
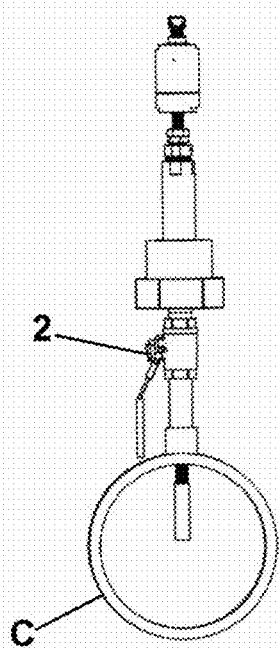

Referring to FIGS. 1A-11B, and 18-21A the preferred embodiment of the present invention contemplates a unique and innovative housing configuration, with substrate coupling and separate bracket for use therewith, shown implemented in conjunction with a self-contained, modular sample/conditioning system mounted at the source of the sample, such as, for example, a pressurized source 1 comprising a pipe or conduit C having mounted thereto a process isolation valve 2 (FIGS. 1A-1C).

As shown in the figures, the substrate coupling 3 has first 31 and second 31' ends, and a length 31", with a passage 33 formed longitudinally therethrough, said passage 33 having an internal diameter (ID) 33' sized for the positioning, i.e. insertion and retrieval, of the extraction device 4 (shown in the form of an insertion probe) therethrough. The second end 31' of substrate coupling 3 has a cylindrical socket 32 formed medially therein having an inner diameter (ID) 32' formed to receive insertion assembly 34 of extraction device 4, the passage 33 having a threaded connection 32" where it opens into socket 32. The second 31' end of substrate coupling 3 has formed about the socket area a substrate coupling bracket mounting area 27, comprising threaded apertures 31, 3b, or slots formed to secure the base 6a of substrate bracket thereto. The cylindrical sidewall 27' of substrate coupling forms the housing engagement area 28, having an outer diameter 28' (OD) formed to facilitate close association or engagement with the inner diameter/perimeter of the mounting aperture formed in the housing/enclosure, as further described herein. Situated below the housing engagement area 28 is substrate coupling base 3' (shown having a hexagonal face for mounting), the base 3' having a width 28" greater than the diameter 28' of housing engagement area, said base orthogonally emanating from said sidewall of said substrate coupling so as to provide an extension 29 or support area, which could be used to support a housing resting thereupon, as will be further discussed herein.

A substrate coupling 3 (FIGS. 2A-2C) is mounted to the process isolation valve 2. The coupling 3 connects the process source 1 to the modular sample system of the present invention (discussed in detail infra) while also allowing for the installation/utilization of an independent, insertable extraction device such as Mayeaux U.S. Pat. No. 8,522,630 probe, the contents of which are incorporated herein by reference thereto.

In the present system, the modular sample/conditioning system cooperatively engages the isolation valve so as to allow for the passthrough of an extraction device 4 (FIGS. 3A-3C), and allows both components to operate independently of one another. An enclosure (14a and 14B in FIGS. 9A-11B) is provided to house the modular components (as further discussed herein), but does not require direct connection or engagement to extraction device 4, as is the case with prior art.

FIGS. 3A-3C and FIGS. 16-21A illustrate the extraction device 4 passthrough ability through the substrate coupling 3 and threaded connection thereto, through open isolation valve 2 to conduit C.

Figure 4A:
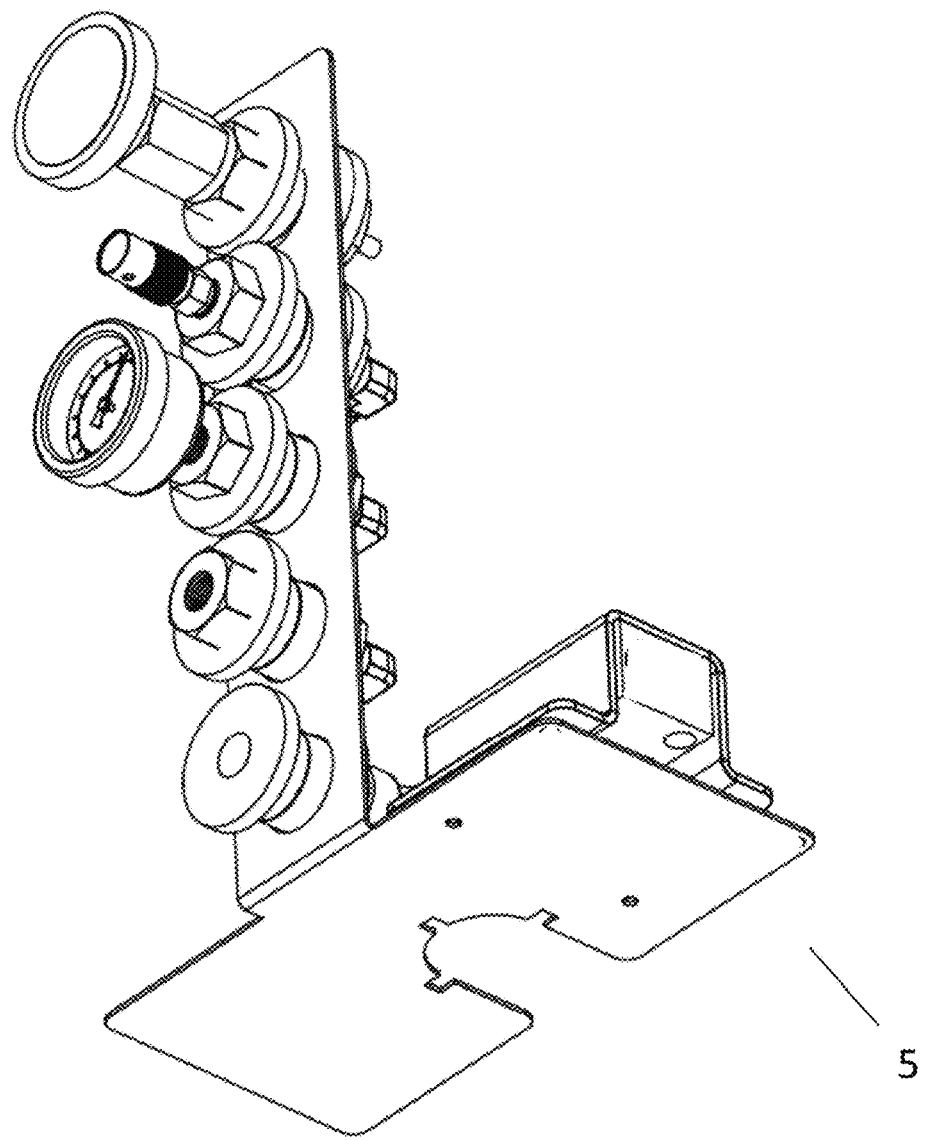
Figure 4B:
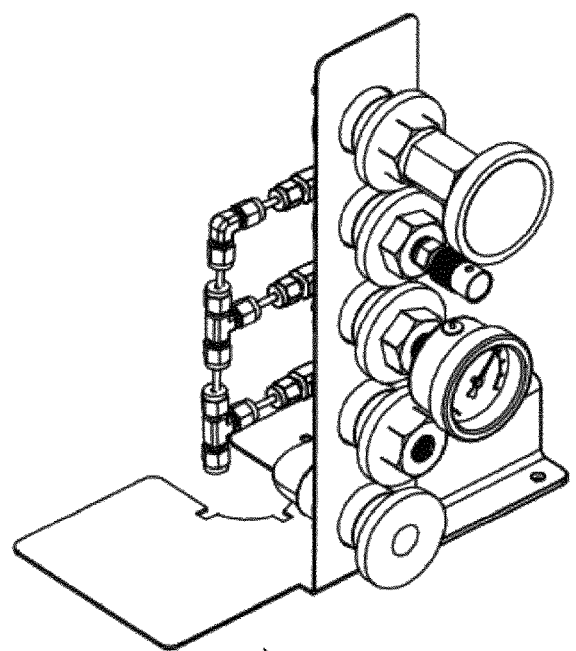

FIGS. 4A-4B illustrate an exemplary the modular sample system 5, comprising multiple diverse sampling and/or conditioning components mounted to a mounting bracket, also referenced as the substrate bracket. The modular sample system 5 can be pre-configured independent of the operation of the extraction device 4, and also independent of the enclosure 14a and 14B, on-site, as required.

Figure 5:
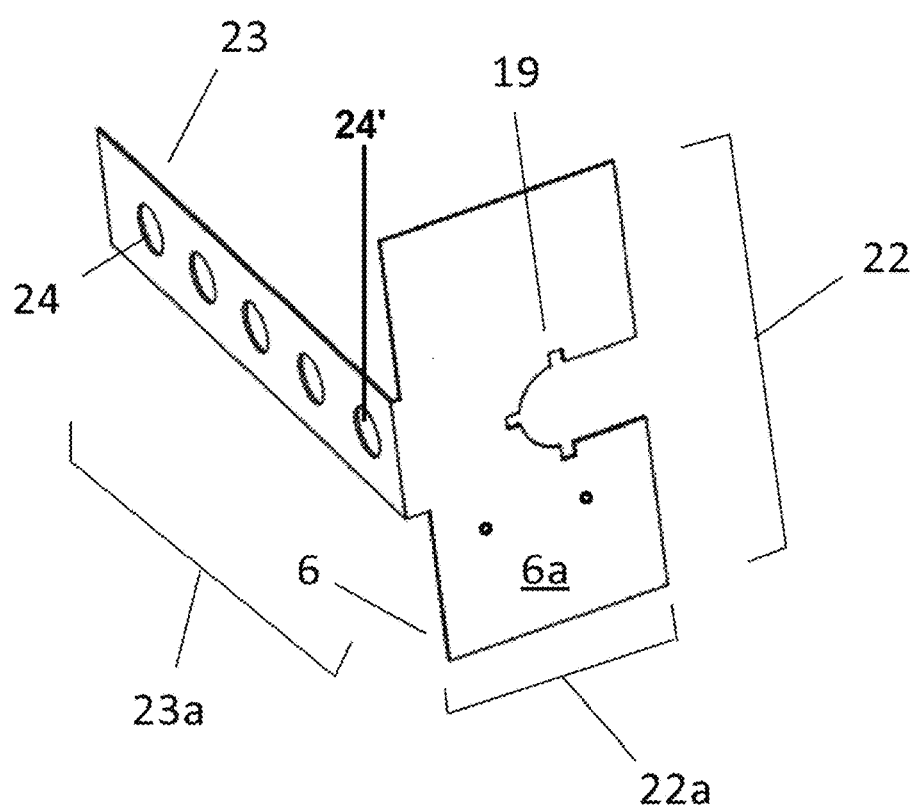
FIG. 5 is an upper, isometric view of the substrate bracket (6) (a/k/a mounting bracket) of the present system.

FIG. 5 illustrates the substrate bracket 6 before the individual modular sample system components are attached and configured on it. The bracket is configured to allow multiple, diverse components to be installed thereto for cooperative flow therebetween, or otherwise, as required.

The bracket holes of the substrate bracket 6 are shown as spaced evenly so that sample system components can be placed and configured in any desired order.

Figure 6A:
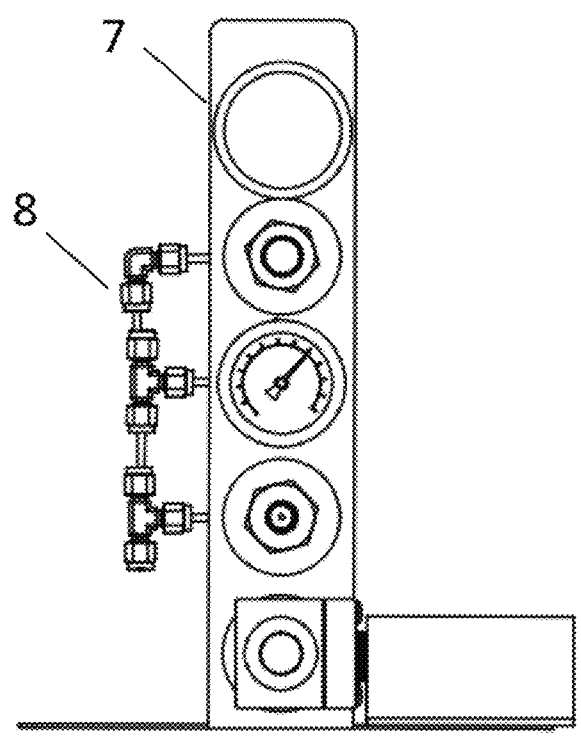
FIGS. 6A and 6b are front and side views, respectively, of the first, preferred embodiment of the present invention, illustrating various exemplary modular sample components forming an exemplary modular sample conditioning system using the substrate bracket (6) or mounting bracket of FIG. 5.
Figure 6B:
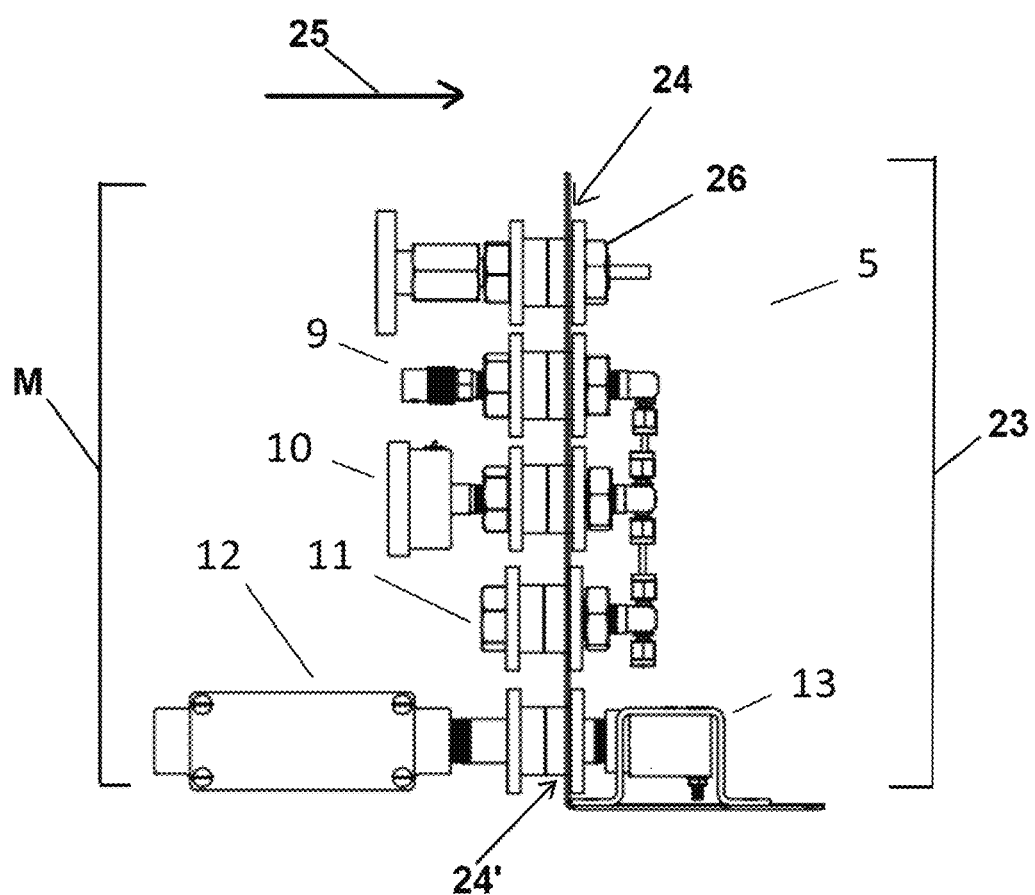

The substrate bracket 6 is formed to readily attach, for example, via threaded mounting apertures 3a, 3b, at the free end of the substrate coupling 3 (FIG. 2C), which forms the substrate bracket mounting area 27 (FIGS. 2A-2C, 21, 21A) of substrate coupling 3. A typical modular sample system 5 configuration is shown in FIG. 6A-6B. This exemplary system is shown incorporating various modular components M, including a temperature indicator 7, with tubing and fittings 8 connecting the various other components in the desired configuration, in the present example a serial flow comprising relief valve 9, a pressure gauge 10, an outlet NPT connection 11, a conduit junction box 12, and a self-limiting heater block 13 as shown. For purposes of discussion, those modular components M mounted to the substrate bracket mounting area 27 will be referred to as "mounted modular components"

Figure 7C:
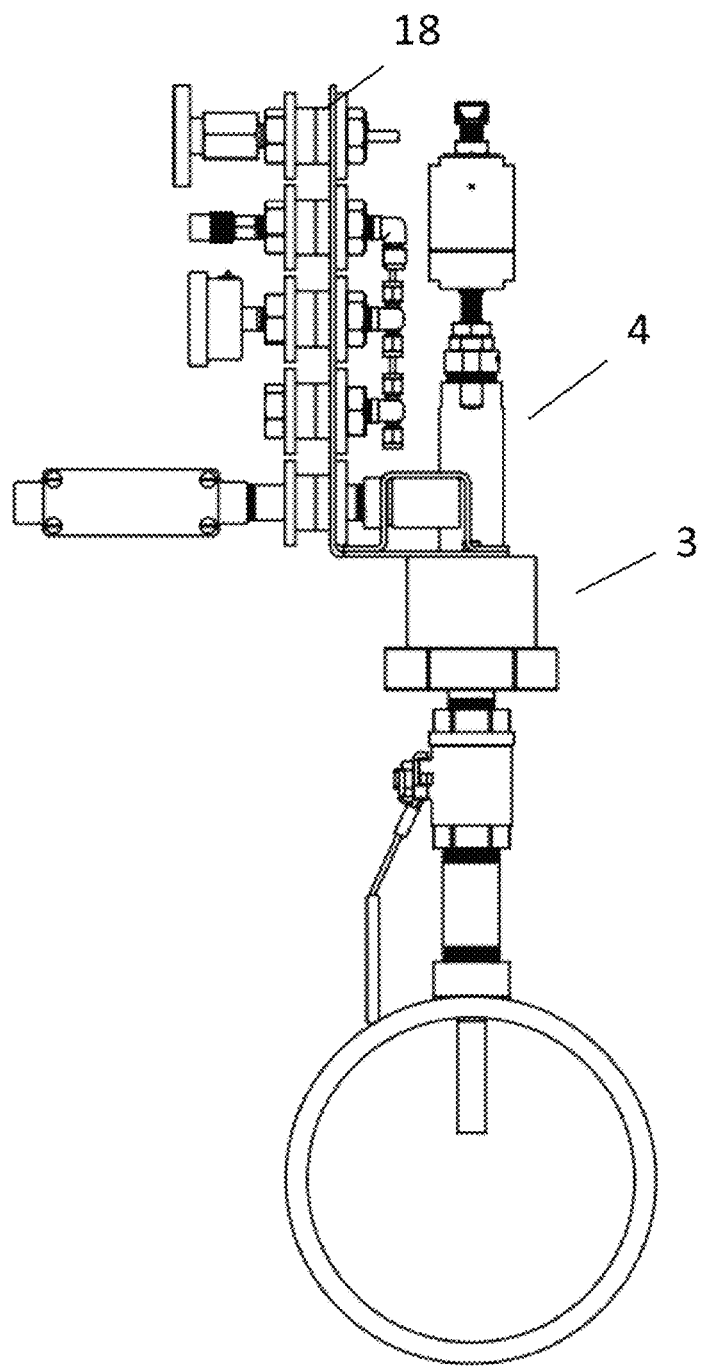
Figure 8A:
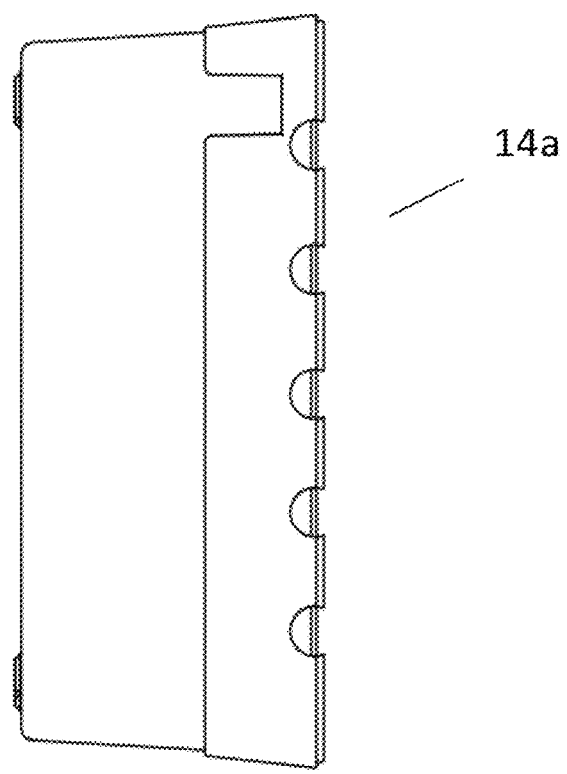
FIG. 8A is a side view of one of two enclosure components of the components which are combined to form the housing of the present invention, the illustrated enclosure shown comprising the housing (approximately split in half along its length) with pre-drilled holes formed therethrough for component access and mounting of the unit.
Figure 11A:
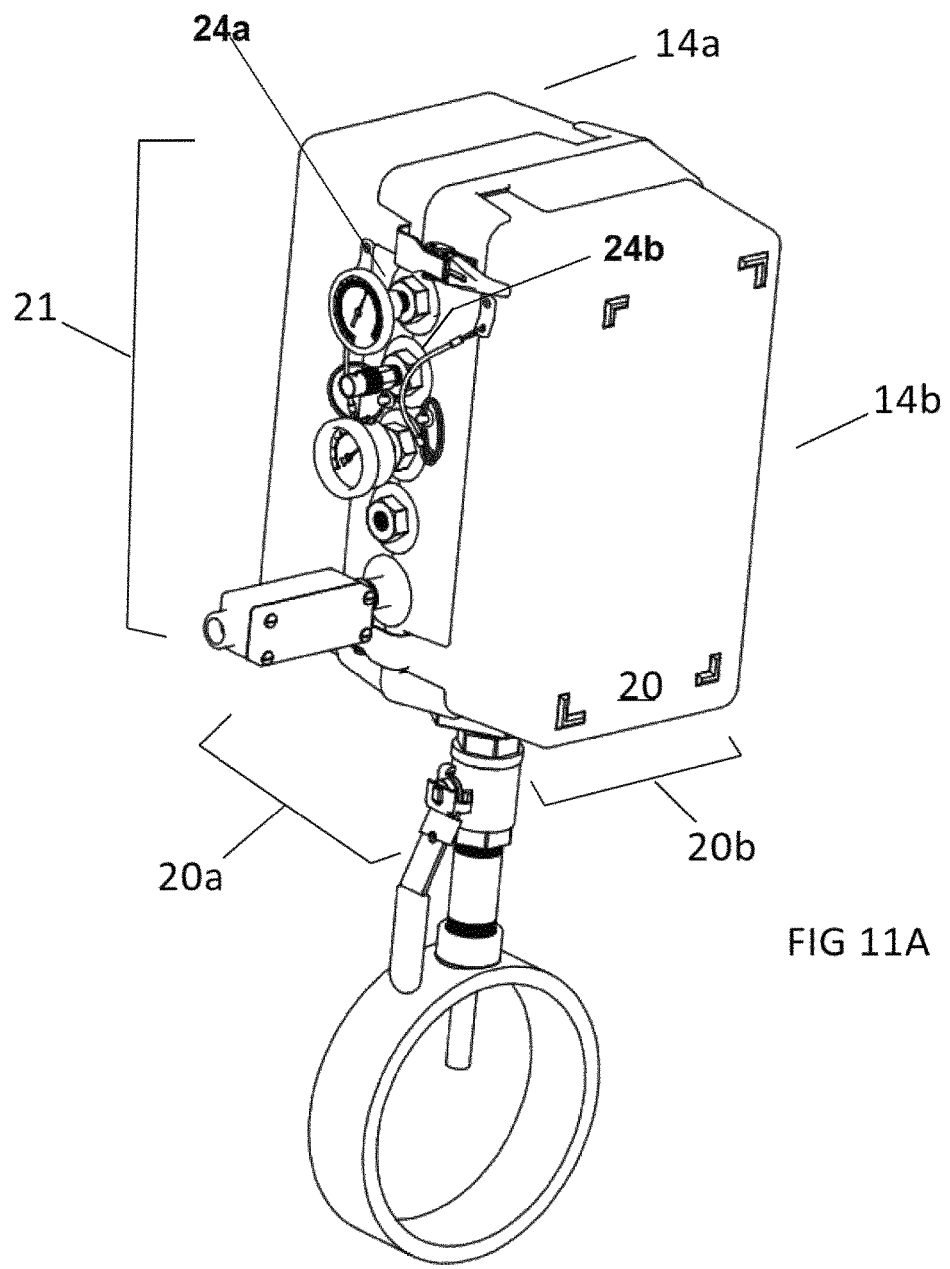
FIGS. 11A-11B are illustrate perspective and end views, respectively, of the housing enclosure enclosing the modular sample system of FIGS. 10A-10C, in a completed installation.

Each of these components are attached to the substrate bracket 6 (FIG. 5), and operate independent of the extraction device 4 (FIG. 7C) and the enclosure 14a and 14b (FIGS. 8A, 8B, and 11A).

Continuing with FIGS. 1-11B, the substrate bracket 6 with sample components is enveloped by the housing formed by enclosure 14a, 14b components to provide a modular sample system which is 100% accessible for service or replacement, with the visible portion of the components as well as those parts of the components for manual control pass through the housing or are otherwise exposed by apertures formed to receive same, as will be further discussed herein.

Figure 7A:
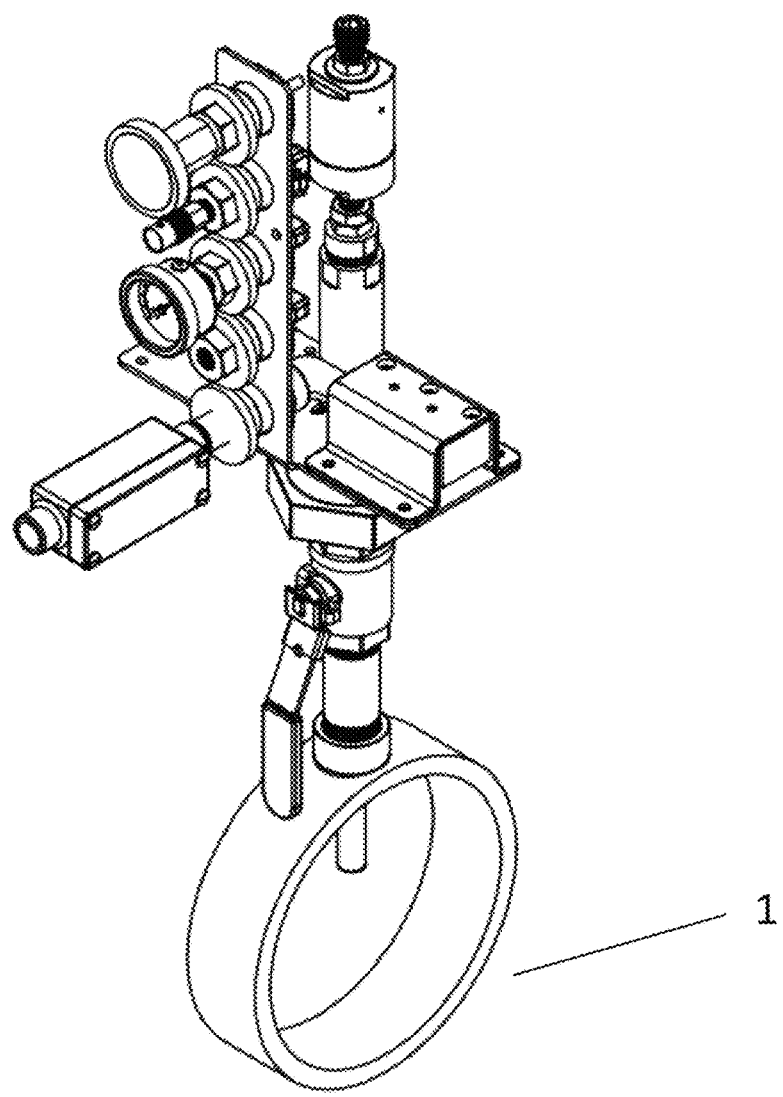
FIGS. 7A-7C are isometric, side, and end views of the exemplary modular sample conditioning system of FIGS. 6A-6B, with the substrate bracket 6 or mounting bracket mounted to the substrate coupling 3 of FIGS. 2A-2C with the extraction device as shown in FIGS. 3A-3C.
Figure 7B:
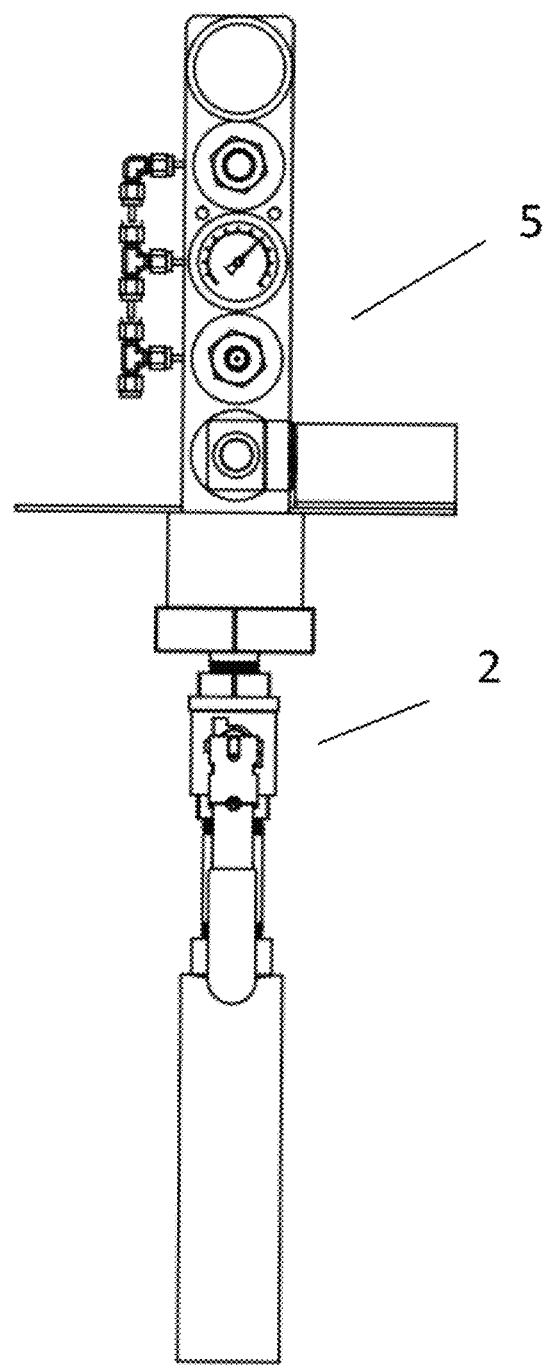

FIGS. 7A-7C shows the pressurized source 1 with the process isolation valve 2 and the substrate coupling 3 and the extraction device 4 and the modular sample system 5. Also shown are the rubber gaskets 18 situated on the components to engage each hole of the bracket. The rubber gaskets 18 ("rubber" is an exemplary material, others may likewise be used), are positioned to engage the edges of one or both enclosures 14A, 14B when brought together at the housing component apertures, and are formed to seal the enclosure 14A, 14B about the components upon which the subject gaskets 18 are mounted, allowing a portion to pass through or other wise be visible/accessible outside of the housing, as well as to help the enclosure slide onto and off of the substrate bracket.

Figure 10D:
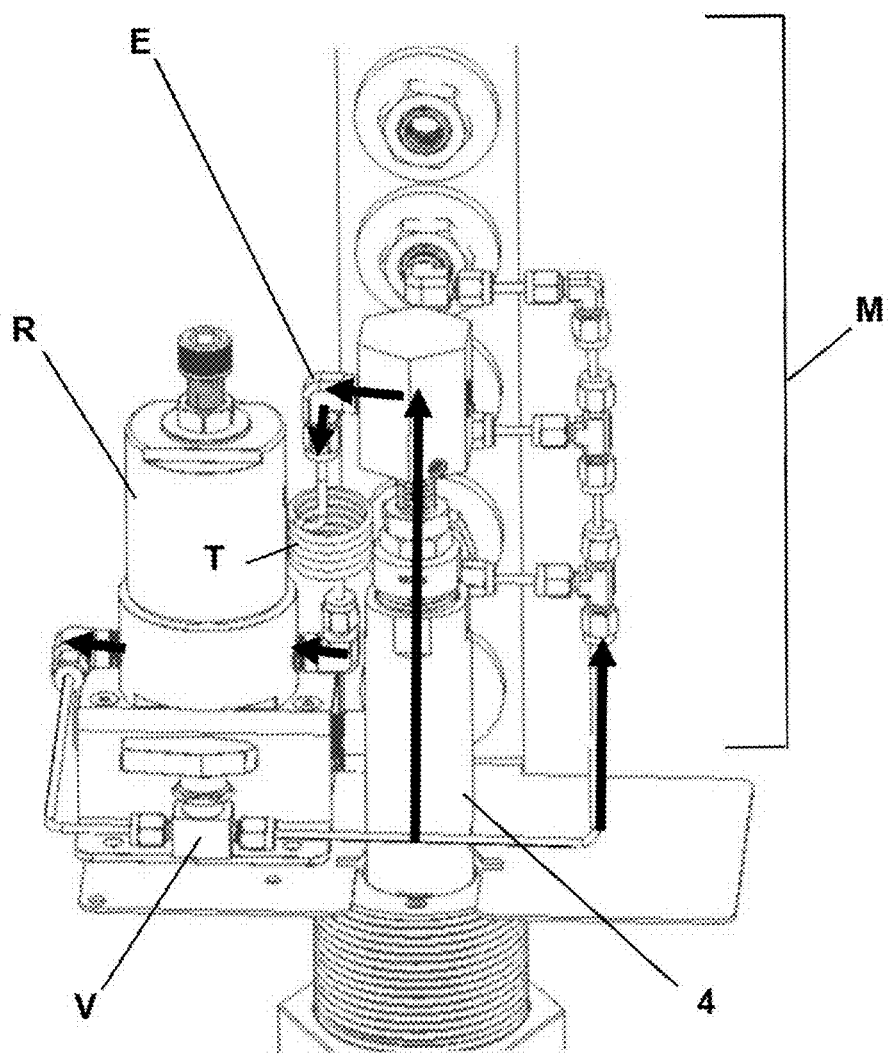
FIG. 10D illustrates a rear view of the modular sample conditioning components of FIG. 10A, illustrating the flow path of the pressurized fluid out of the extraction device 4, through an elbow to a tube T (coiled to allow positioning) leading to a regulator R, then out through a valve V, to the modular components M.

FIGS. 8A, 8B, 10a-10c, and 12B shows a side 36' of first enclosure half 14a and second enclosure half 14b (also referred to as enclosure components) having formed or pre-drilled therethrough passages or holes forming module component access apertures 24a, 24b which, when the first 14a and second 14b enclosure halves are combined, forms a housing 20 having a series of holes or passages formed to encircle a portion of respective mounted modular components partially protruding therethrough for user access or monitoring, as well as providing a free-floating mounting of the housing to the modular conditioning system (i.e., a housing enveloping the substrate coupling, substrate bracket, and modular components mounted thereto, without the need for fasteners or the like to directly secure the housing to the enclosed system) while stabilizing same, as will be further discussed herein. The module component access apertures 24a are evenly spaced so that sample components can be arranged in various different orders or configurations. The holes formed in the side walls of the housing preferably align or coincide with those formed along the substrate bracket and the mounted modular components associated therewith. The enclosure slides onto and off of the rubber gaskets 18 at the substrate bracket. The enclosure is shown using alignment pins 17 to align the two enclosure halves 14a, 14b so that the module component access apertures 24a, 24b formed in the assembled housing 20 align with the module component mounting apertures 24, 24' situated on substrate bracket, and said enclosure halves 14a, 14b forming housing 20 are held in place with clasps 15, as shown in FIGS. 10A-10C.

Continuing with FIGS. 2A-2C, 8A, 8B, 11B, 12B and 19-21A, the first 14a and second 14b enclosure halves forming housing 20 are formed to provide a mounting aperture 30 at the lower, centered, end 36 of the housing formed to allow the passage therethrough of the substrate coupling 3 in the vicinity of the substrate housing engagement area 28 of substrate coupling. In the preferred embodiment of the present invention as shown, the mounting aperture 30 has a diameter 30' formed to encircle or engage the housing engagement area 28 of substrate coupling, as well as utilize the edge forming the mounting aperture 30 of the housing, or gasket 18a associated with said edge of the housing, to rest upon the extended edge or extension 29 formed by the greater OD of base 3', utilizing same as a support surface, as well as a means of further stabilizing and anchoring the housing to the system.

Figure 9A:
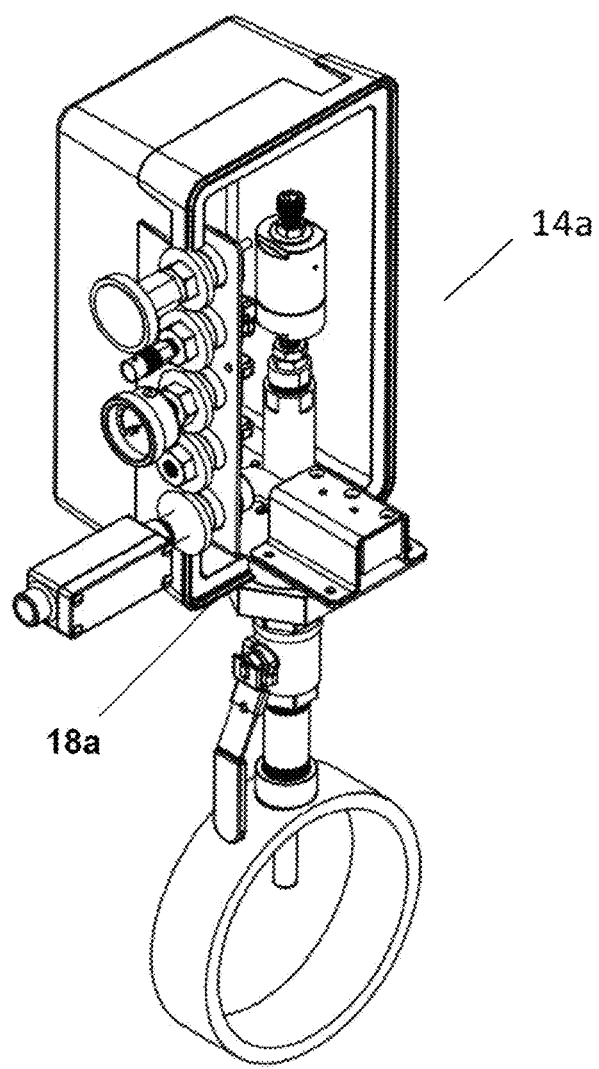
FIGS. 9A-9C are isometric, side and end views, respectively, of the mounted sample conditioning system comprising modular sample conditioning components substrate bracket 6 or mounting bracket of FIGS. 7A-7C, with the bracket housing/enclosure of FIGS. 8A-8B mounted thereto.
Figure 9B:
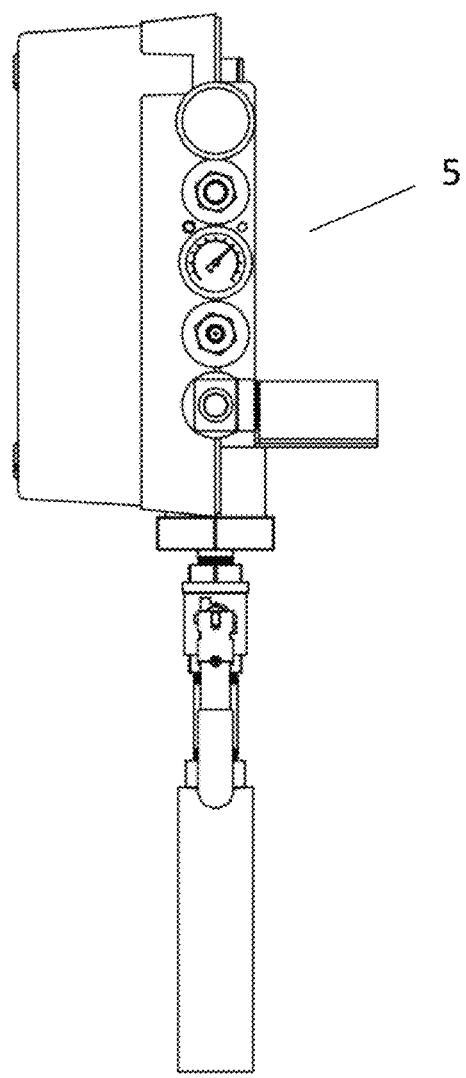
Figure 9C:
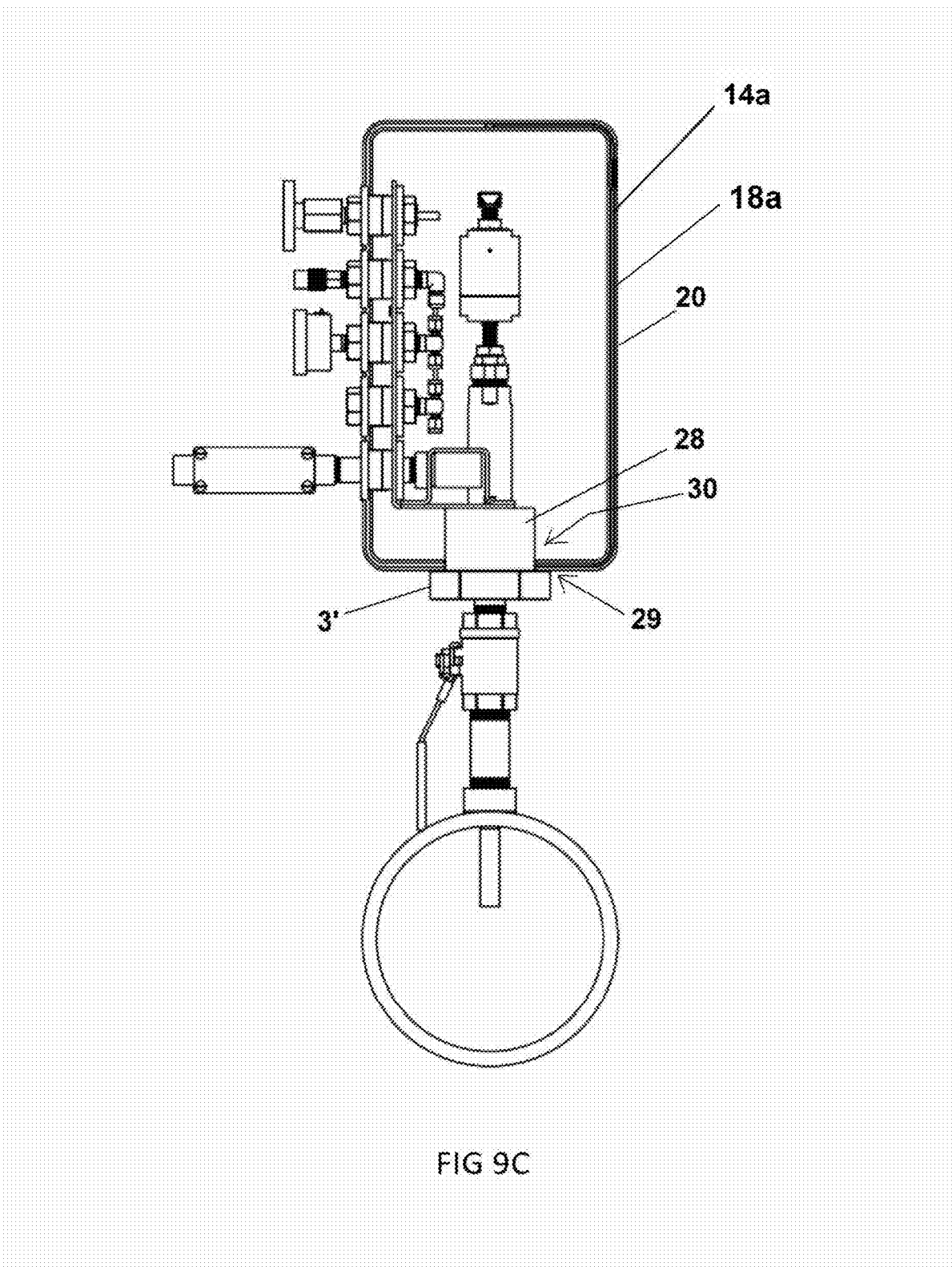

FIGS. 9A-9C shows one half of the enclosure 14a engaging the substrate bracket 6, modular components and substrate coupling 3, with the other enclosure 14b not yet installed, revealing the system being half enclosed. Each half of the enclosure is completely independent and is held in alignment with the substrate bracket using the pin 17 for that half. The other half of the enclosure 14b can hang from the substrate bracket using its pin 17 as shown in FIGS. 10A-10C.

The pins 17 are used for alignment when the enclosure is in place or to hold the enclosure temporarily as shown in FIGS. 10A-10C, when service or maintenance is required. Both halves of the enclosure 14a and 14b may be removed at the same time or installed at the same time or used one at a time independently, thereby allowing 100% access to the modular sample system for service or replacement.

The modular sample system can be completely replaced with a spare unit (another modular sample system 5) in the field as required, or worked on at a component level with the component being repaired or replaced. This innovation allows a less skilled technician to operate in the field and a more skilled technician to operate back at the company home base or central service location.

FIGS. 10A-10C shows the enclosure halves 14a and 14b on the substrate bracket fitting around the gaskets 18 aligned to the substrate bracket with pins 17 and held in place with clasps 15. As shown, pins 17a, 17b are attached to enclosure halves (14a and 14b) with cables 16 to align and retain the enclosure halves forming the housing 20 or enclosure.

Figure 11B:
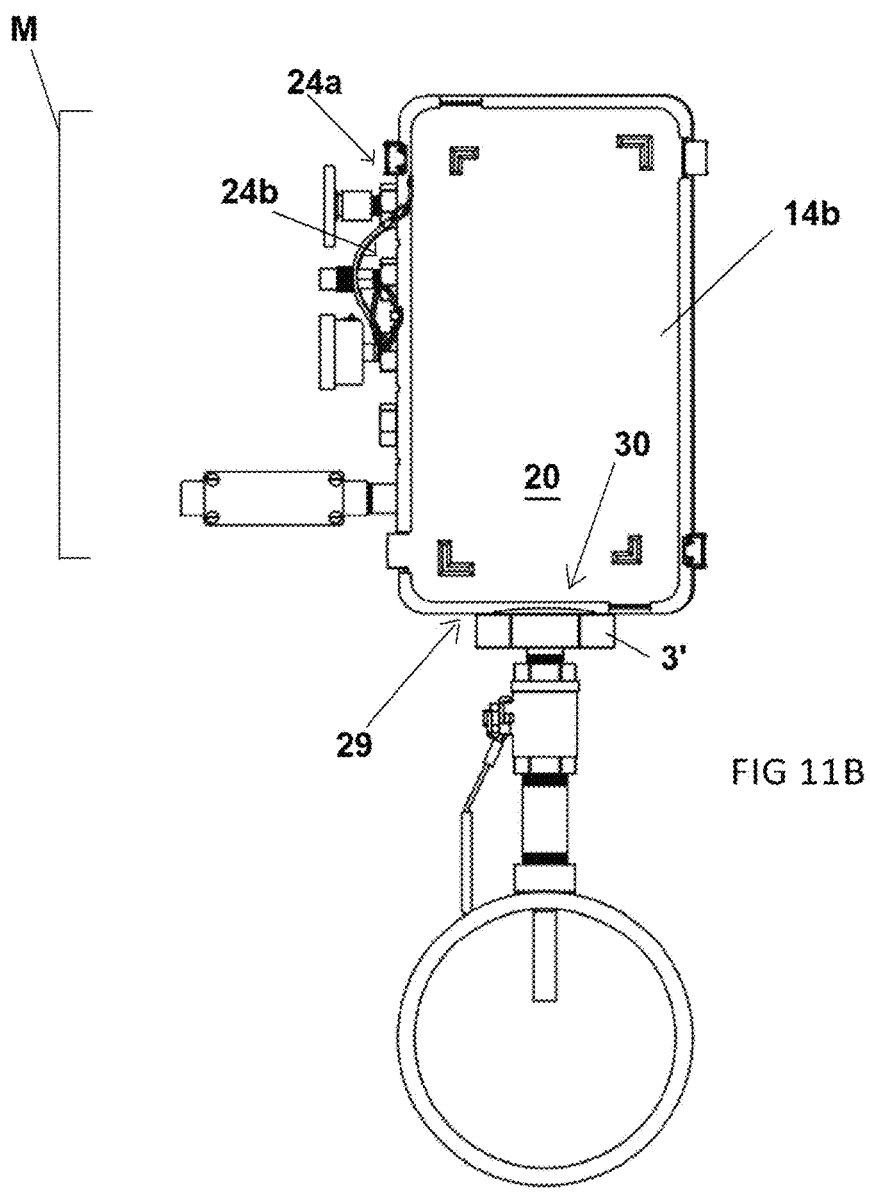

FIGS. 11A, 11B show the completed modular sample system in the preferred embodiment, at the site of the pressurized gas source. The alignment pins (FIGS. 10A-10C) ensure that each housing or enclosure half 14a, 14b, is properly aligned with the docking platform. This feature also helps to ensure that the enclosure halves will not move due to pipeline vibrations. The same alignment pins are also used to hang the enclosure halves when service or maintenance is performed (FIG. 10C). This feature is useful to keep the enclosure half handy (within reach) and off the ground but also out of the technicians: way.

The housing formed by the joined enclosure halves (14A, 14B) with the openings are positioned and formed to engage the modular components where access outside the housing of parts of the modular components is desirable, providing visible components. Most components utilized in analyzer sample conditioning applications may be adapted for exterior use, even those not necessarily specific to natural gas or gas chromatography.

The visible components can be placed in any order that the application would require. The hole spacing (the holes formed in the housing by enclosures (14A, 14B) are preferably evenly spaced so the visible components may be placed in any order that makes sense for the particular application.

Exemplary modular components MC wherein visibility or other access exterior the housing would be advantageous for analyzer sample conditioning, for example, might comprise (in no particular order), pressure gauge(s), temperature gauge(s), outlet fitting(s), relief valve(s), and conduit connection, and the present system allows technician/operator access the exposed modular components external the enclosure or housing without having to open/disassemble same.

By allowing visibility access exterior the housing, the technician is able to read the pressure gauge, temperature gauge and other important data readings, as well as access the outlet fitting and inspect the conduit wiring and know that the relief valve is not activated. Other components such as tubing, fittings, valves, and any other conditioning components needed are not visible, remaining in the housing formed by enclosure components 14a, 14b, since they only need to be accessed for service or maintenance.

The present invention thereby provides visibility of components such as pressure gauge, temperature gauge, relief valve, outlet fitting, and conduit fitting without having to open or disassemble the enclosure (housing). This feature is in contrast with the prior art, which teaches a housing enclosure with pressure gauge and sight glass inside the enclosure as previously discussed. Unlike the prior art, the modular components in the present case can be arranged on the mounting bracket in any order using the substrate bracket design and matching enclosure design (housing) of the preferred embodiment of the invention.

Accordingly, with the housing formed by the enclosure components 14a, 14b (FIG. 11A) the preferred embodiment of the present invention, the modular sample system 5 (FIG. 9) is protected from the environment (via the housing) and can be temperature regulated or controlled, and yet the gasketed openings of the housing are formed to engage the periphery of desired components to provide exterior access/ visibility of said components that require said access for operation.

This arrangement can accommodate a diverse selection of components such as electronic, electrical, flow control, etc. mounted into a non-customized substrate (the substrate bracket or mounting bracket) and housing (formed via enclosure components 14a, 14b), while allowing the components to be easily mounted into a customizable configuration along with protection from the environment and visibility of certain components, while providing 100% access to all components AND tubing when one or both enclosure components 14a, 14b forming housing are removed, while maintaining the rigidity of the system and not having to break any fittings or connection, or disassemble the system.

The present design is unique in that the substrate/mounting bracket is designed to structurally integrate with the two enclosure halves forming the housing and the mounted modular components so that, when assembled together, the structure integrated to substantially enhance rigidity, allowing mounting to the pressurized source via the unique substrate coupling 3, while allowing the extraction device 4 to pass through, in a stable overall structure.

To accomplish this enhanced structural rigidity, the configuration of the substrate bracket 6 is formed to have base 6A width 22 and depth 22a dimensions (FIG. 5) to closely approximate the interior width 20a and depth 20b of the base 20 of the enclosure formed by the combining of enclosure components 14a, 14b (FIG. 11A).

Further continuing with FIGS. 4-5, 11A, and 8A-9C, laterally emanating from the base 6A of the substrate bracket is module mounting area 23, which has formed therethrough multiple module component mounting apertures 24, 24', shown in generally uniform spacing along its length, said module mounting area having a length 23a formed to generally span the longitudinal length 21 (in the present example, along a sidewall) of the interior of the housing formed by assembled enclosure components 14a, 14b, so that the module component mounting apertures 24 are aligned with the module component access apertures 24a, 24b formed by the joined enclosure halves 14a, 14b.

When assembled, coupling 3 is mounted to process isolation valve. Insertion probe 4 is then mounted to substrate coupling 3 via threaded connection, then a portion of its length passes through substrate coupling passage, through open isolation valve 2. Substrate bracket 6, which can have the modular components already mounted thereon forming the sample system 4, is mounted to coupling 3. Referring to FIGS. 5, 6a-6b, 9A-9c, 11A, and 12C, modular components, which can vary depending on the application but might comprise, such as previously discussed, for example, a block heater 13, conduit junction box 12, NPT connection, 11, pressure gauge 10, relief valve 9, temperature indicator 7, or the like, each having a role in the conditioning, monitoring, or control of the sample, pass through 25 and engage via threaded connectors 26 or the like, the module component mounting apertures 24, 24'. Module component access apertures 24a, 24b, are formed about the respective modular components when the enclosure halves 14a, 14b are joined to form the housing with the access aperture 24a, 24b as they are positioned to encircle the respective mounted modular components. Accordingly external access to various mounted modular components is provided upon the joining of enclosure halves 14a,14b to form housing 20. Simultaneously, the mounting aperture 30 at the lower end of the enclosure halves 14a, 14b forming housing are positioned to engage the cylindrical outer wall of the substrate housing engagement area 28 with said enclosure halves 14a, 14b being joined. The combined engagement of the engaged enclosure halves forming housing with the exposed modular components (which components are mounted to the substrate bracket) via component access apertures 24a, 24b and the engagement of the mounting aperture 39 about substrate coupling 3 thereby provides a structural integration with the mounting of the enclosure or housing to the system which enhances stability as well as the rigidity of the mount, while providing a "floating" case which envelopes and protects the modular sample system 5 without the need to affix the housing rigidly thereto, as the present system does not use or require fasteners to affix the housing structure directly to the system which it encloses, instead utilizing the housing configuration itself to engage said mounted modular components (via said modular component apertures) as well as the substrate coupling (via mounting aperture 30) to engage the lower wall of said housing about said substrate coupling. The present system thereby provides easy and full open access to the interior of the housing/enclosure and associated modular components or the like sheltered therein (components shown mounted to substrate bracket), by simply separating and removing enclosure halves 14, 14b.

The base substrate (bracket) mounts to the substrate coupling via substrate coupling engagement slots 19, which are formed to align with threaded passage 3b formed in base 3a of substrate coupling 3.

Accordingly, in the preferred embodiment of the invention, the horizontal portion of the base substrate (rectangular base) has dimensions that approximate the interior base of the enclosure. Also, the vertical portion of the base substrate spans the length of the enclosure. This design makes the sample system rigid and independent of the enclosure (i.e. able to "stand alone") allowing 100% access to all components and tubing for service, maintenance, and replacement.

Conversely, the prior art has used a backplane or panel that was fastened to the back of the enclosure. Components were fastened to the panel and were only accessible if the cover was unbolted or opened. The present invention overcomes these issues.

Figure 12A:
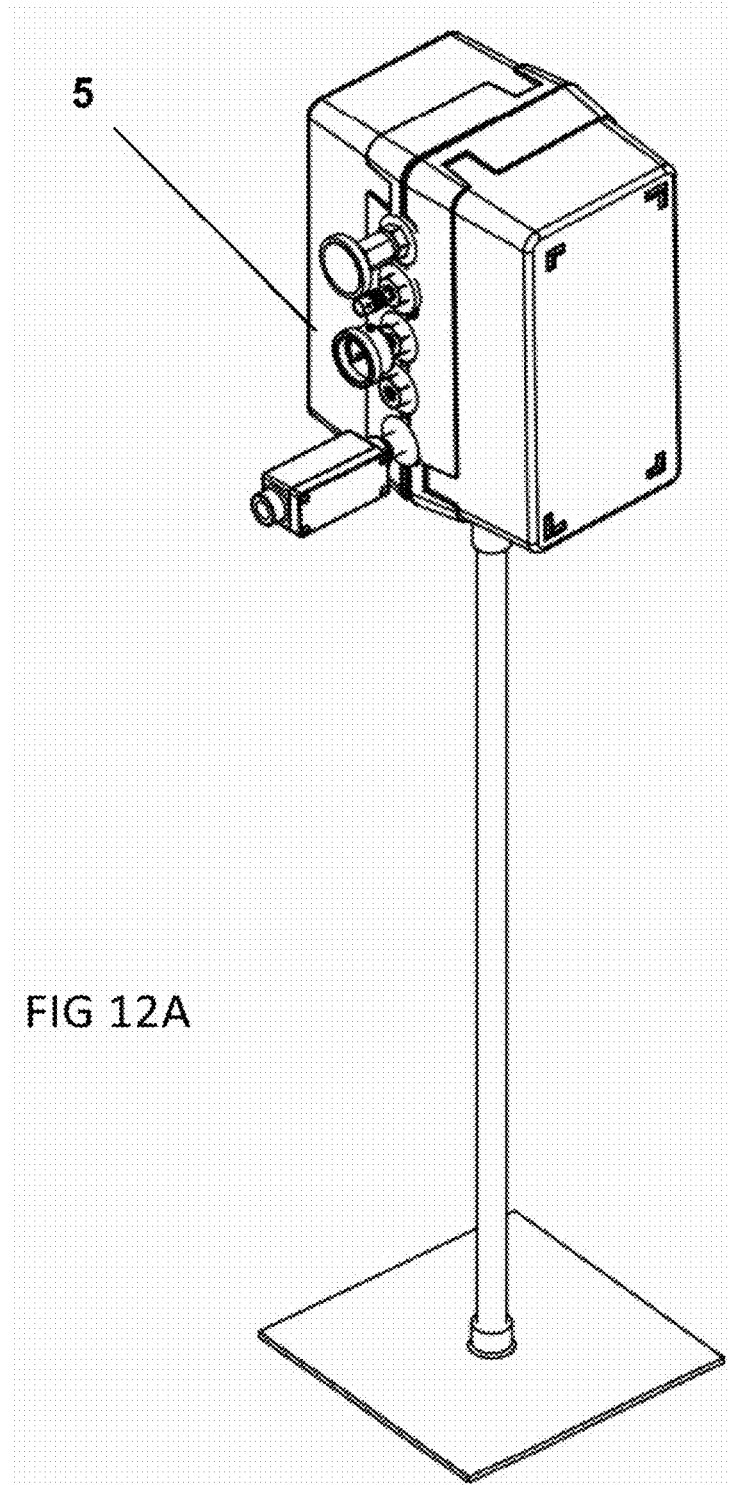
FIGS. 12A and 12B are perspective and frontal views, respectively, of a second, alternative embodiment of the present invention, illustrating the housing enclosure enclosing the modular sample system as a stand-alone location situated between the source and the analyzer.
Figure 12B:
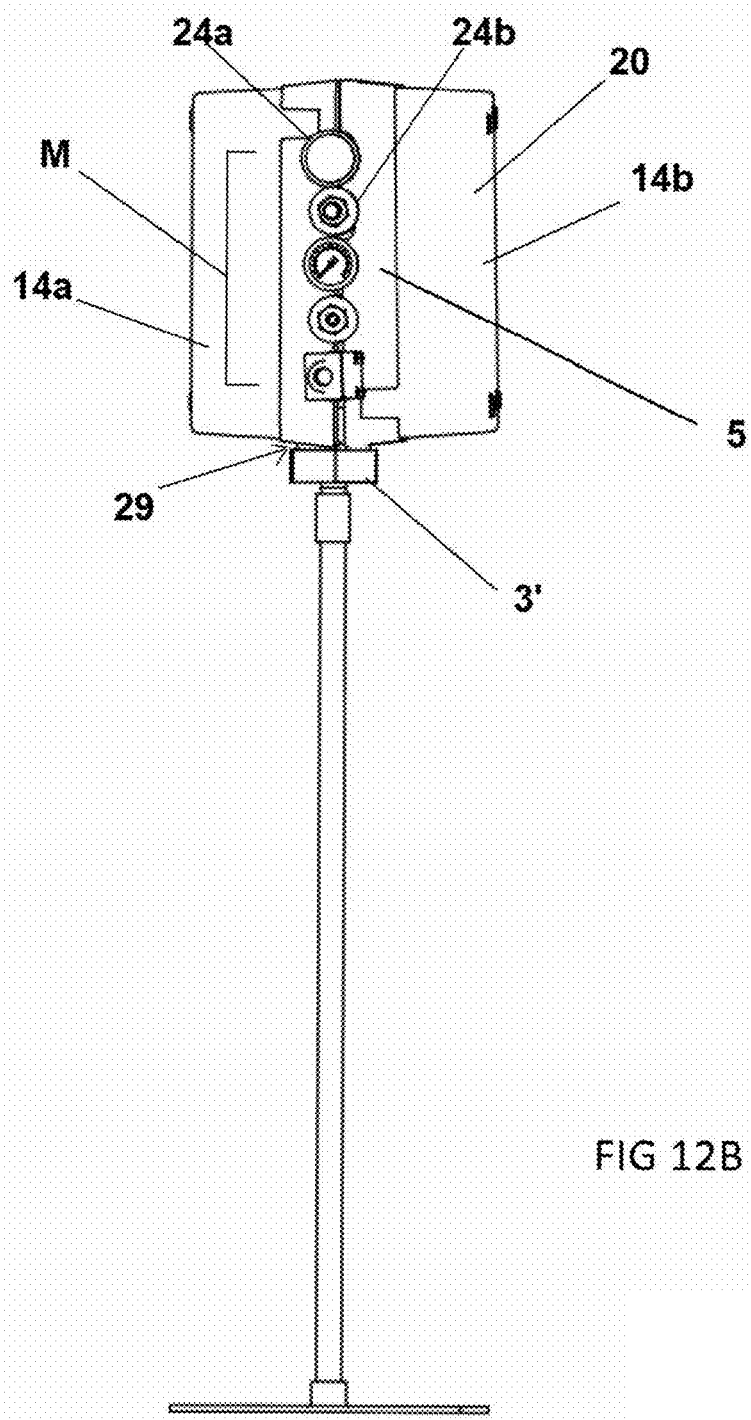

A second embodiment is shown in FIGS. 12A-12B, where the modular sample system 5 is not required to be situated at the pressurized source but is instead at a stand-alone location between the source and the analyzer. All of the benefits and features described above would apply to this location as well. It may be desirable to have one modular sample system at the pressurized source with one configuration and a second modular sample system with a different configuration between the source and the analyzer.

Figure 13:
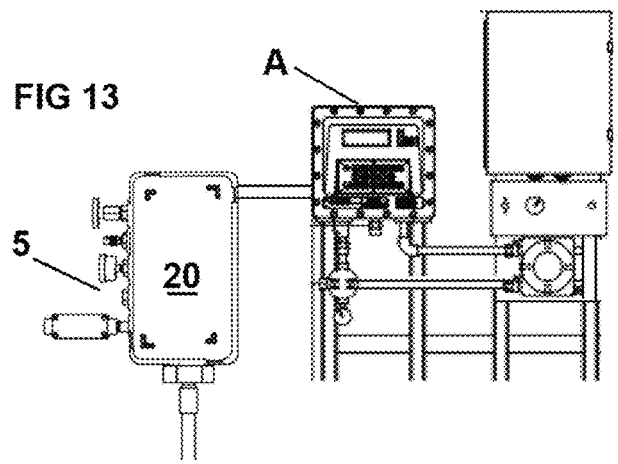
FIG. 13 is a frontal view of a third, alternative embodiment of the present invention, wherein the modular components are mounted on the substrate bracket/mounting bracket and enclosed by the housing/enclosure, at the location of and just prior to a stationary analyzer.

A third embodiment is shown in FIG. 13, where the modular sample system is used at the same location as the stationary analyzer A.

Figure 14:
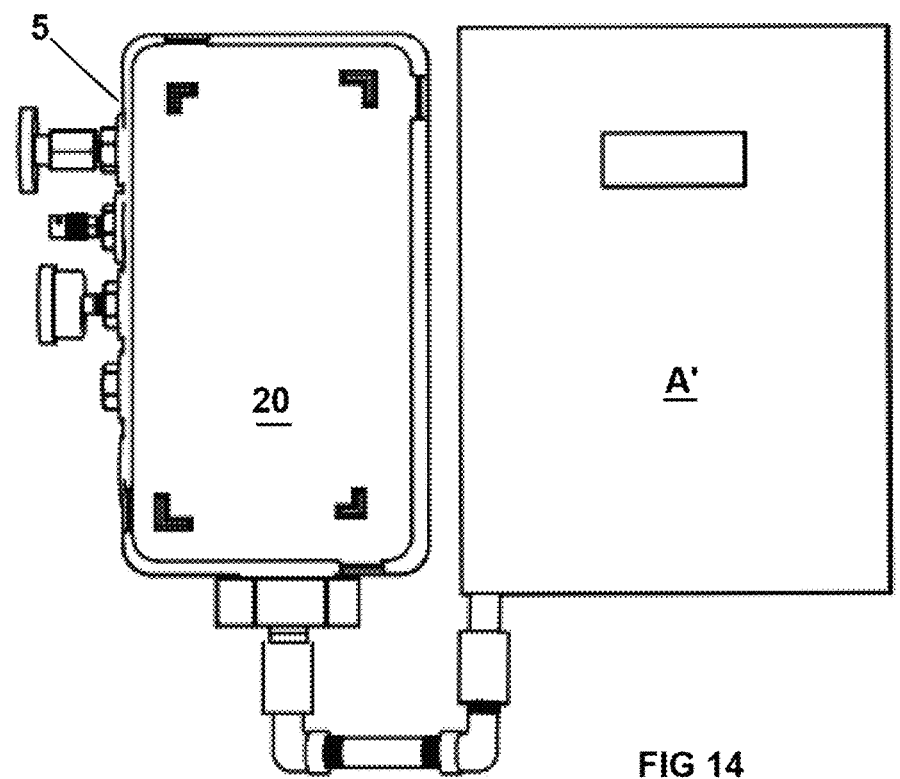
FIG. 14 illustrates a side view of still other embodiments of the present invention illustrating the modular sample system of the present invention integrated with a portable analyzer.
Figure 15:
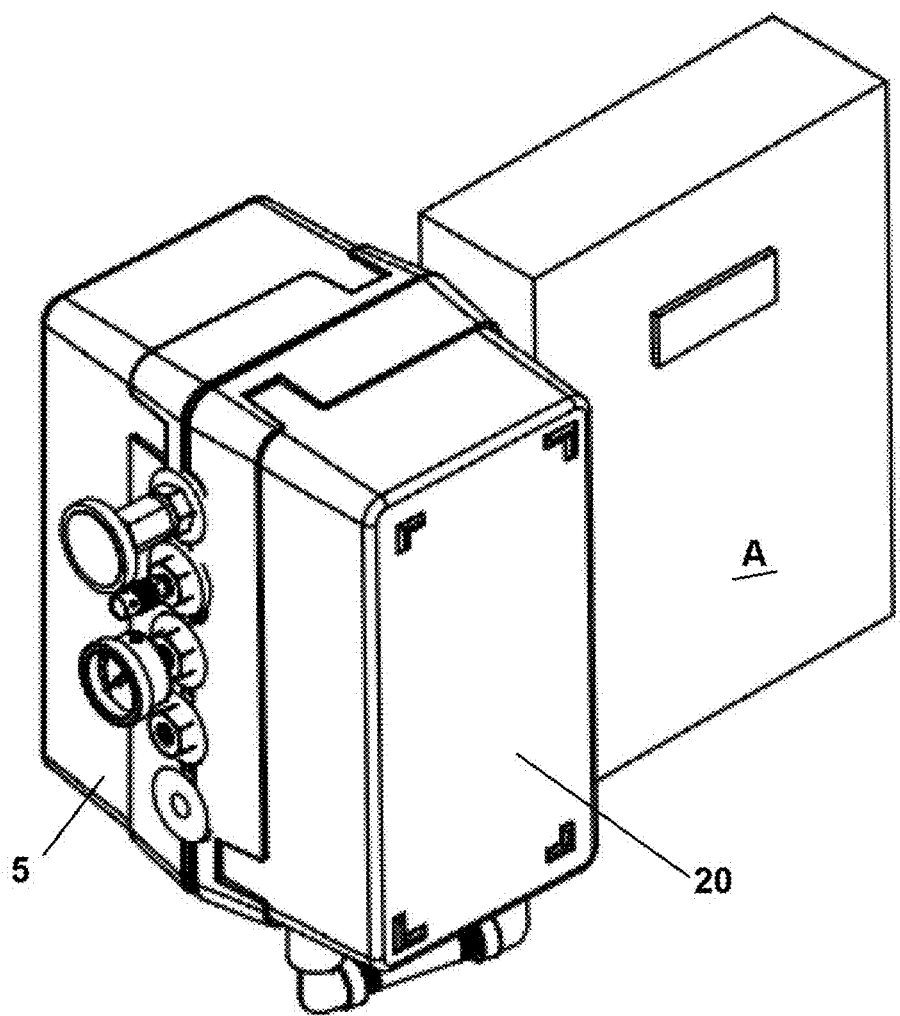
FIG. 15 is an isometric view of the invention of FIG. 14.

Other embodiments could include the modular sample system integrated into a portable analyzer A', as shown in FIGS. 14-15.

Based upon the above and foregoing, a method of providing a modular sample conditioning utilizing the present system may comprise, for example, the steps of:

a. providing a substrate coupling formed to engage a fluid passage, said substrate coupling formed to selectively facilitate the passage of an extraction device therethrough;

b. mounting said substrate coupling to a process isolation valve that is mounted to a conduit containing a pressurized fluid;

c. mounting a substrate bracket to said substrate coupling, said substrate bracket having emanating therefrom a module mounting area having a length;

d. mounting one or more modular components along the length of said module mounting area;

e. providing fluid from said fluid extraction device to said modular components;

f. facilitating the passage of said fluid extraction device through said substrate coupling to engage the pressurized fluid;

g. facilitating the flow of fluid from said fluid extraction device to said modular components;

h. using first and second enclosure components to engage said substrate coupling to enclose same, forming a housing, while i. allowing portions of said modular components to pass through said housing, providing exterior portions of said modular components outside of said housing for visibility and access.

ELEMENTS 1 pressurized source
2 process isolation valve
3, 3', 3a, 3b substrate coupling, base, threaded mounting apertures
4 extraction device (as probe)
5 modular sample system
6, a substrate bracket, base
7 temperature indicator
8 fittings
9 relief valve
10 pressure gauge
11 NPT connection
12 conduit junction box
13 block heater
14a,b enclosure halves
15 clasps
16 cables
17 pins
18, 18a gasket, gasket
19,a substrate coupling engagement slot
20, a,b enclosure base width, depth
21 enclosure length
22 base width, depth
A, A' Analyzer
C Conduit
M Modular Components
E Elbow
R Regulator
T Tube
V Valve
23, a module mounting area, length
24, 24' 24a, 24b module component mounting apertures, access apertures
25 Pass through
26 Threaded Connector
27, 27' Housing Mounting Area (on substrate coupling), cylindrical sidewall
28, 28', 28" Substrate Coupling Housing Engagement area, width/diameter, base width/diameter
29 Substrate coupling base extension
30, 30' Mounting aperture for engaging substrate housing engagement area, width
31, 31', 31" substrate coupling first, second ends, length, diameter
32, 32', 32" Substrate coupling socket, passage, threaded connection
33, 33' substrate coupling, threaded nipple
34, 34', 34" insertion assembly of extraction device 4, threaded end
35, 35' insertion retrieval
36, 36' end, side of housing enclosure
- - -

The embodiments listed are not intended to be an exhaustive list of applications, but only intended to show the need and some of the practical applications of the invention. Further, the invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

I claim:

1. The method of housing a modular sample system, comprising the steps of:

a. providing a substrate coupling having a length and first and second ends, and a passage formed therethrough to receive a fluid extraction device, said substrate coupling having a bracket mounting area at said second end of said substrate coupling, said substrate coupling having a sidewall formed along said length;

b. mounting said first end of said substrate coupling so that said passage of said substrate coupling engages a process isolation valve that is mounted to a conduit containing a pressurized fluid;

c. mounting a substrate bracket to said bracket mounting area of said substrate coupling, said substrate bracket having a module mounting area;

d. mounting one or more modular components along said module mounting area of said substrate bracket, providing mounted modular components;

e. providing first and second enclosure components having sides and an end, each said first and second enclosure components configured to engage one another to provide a housing, said housing having one or more module component access apertures formed to encircle one or more of said mounted modular components, and a mounting aperture formed to engage said substrate coupling;

f. mounting and securing said housing, comprising the steps of positioning said first and second enclosure components about said substrate coupling and substrate bracket, and assembling said first and second enclosure components so as to form said housing, so that said mounting aperture of said housing is situated around said sidewall of said substrate coupling, and said substrate coupling mounting area is enclosed by said housing; while g. aligning one or more of said module component access apertures formed in said housing to engage one or more of said mounted modular components so as to provide exterior access to said mounted modular components outside of said housing.

2. The method of claim 1, wherein in step "g" said step of combining said first and second enclosure components comprises utilizing said one or more of said module component access apertures formed in said housing to engage said one or more of said mounted modular components, so as to support and retain said housing in place.

3. The method of claim 2, wherein there is in step "d" the step of providing a fluid extraction device having a length, and engaging same to said substrate coupling by positioning a portion of said length through said substrate coupling passage, providing a mounted extraction device, and there is further added the step "i" of removing at least one of said enclosure components to provide access to said mounted extraction device.

4. The method of claim 3, wherein said fluid extraction device is a sample probe.

5. The method of claim 3, wherein said housing is insulated, and there is provided after step "h" the added step "i" of heating said enclosure utilizing heat trace tubing from an analyzer.

6. The method of claim 1, wherein in step "d" said modular components comprise modular sample components, and wherein there is provided the added step "h" of facilitating the flow of fluid from said modular sample components to an analyzer.

7. The method of claim 6, wherein said modular sample components comprise modular sample conditioning components, and wherein in step "h" there is added the step of using said modular sample conditioning components to condition said pressurized fluid, providing conditioned sample fluid, and directing said conditioned sample fluid to said analyzer.

8. The method of claim 1, wherein in step e there is further included the step of providing a gasket along said one or more module component access apertures formed in said housing, and step "g" includes the step of utilizing said gasket to facilitate engagement of said housing to one or more said mounted modular components via said one or more module component access apertures.

9. The method of claim 8, wherein in step c said substrate bracket mounting area has module component mounting apertures formed along its length to receive said modular components, and said module component access apertures formed in said enclosure components are in alignment with said module component mounting apertures when said housing is mounted in steps f and g.

10. The method of claim 9, wherein there is provided the added step "j" of utilizing said exterior access to monitor and control the flow of fluid to said modular components.

11. The method of claim 9, wherein there is provided the added step "i" of securing said enclosure components to one another via pins to selectively form said housing.

12. The method of claim 9, wherein there is provided the added step "i" of securing said enclosure components to one another via clips to selectively form said housing.

13. The method of claim 1, wherein in step "a' said substrate coupling has orthogonally emanating from said sidewall, in the vicinity of said first end, a substrate coupling base, and step "f" further includes the step of positioning said housing so that said mounting aperture of said housing encircles said sidewall, above said substrate coupling base.

14. A modular sampling system for retrieving a sample from a pressurized gas source, comprising:

a substrate coupling having first and second ends and a sidewall, said first end formed to engage a process isolation valve in fluid communication with a pressurized fluid, said substrate coupling formed to allow the selective passage of an extraction device therethrough to engage said pressurized gas source;

a mounting bracket having a base engaging said second end of said substrate coupling, said mounting bracket having emanating therefrom a module mounting area having a length;

one or more modular components mounted along said length of said module mounting area of said mounting bracket so as to provide mounted modular components, said mounted modular components having fluid communication therebetween pursuant to a desired flow path, said modular components formed to receive fluid from said extraction device;

first and second enclosure components formed to engage to form a housing, said housing having formed therein one or more module component access apertures for receiving portions of one or more of said modular components therethrough, so as to facilitate exterior access of said one or more modular components outside of said housing, said housing further having formed therein a mounting aperture formed to engage said substrate coupling;

whereby, upon positioning said first and second enclosure components about said substrate coupling and substrate bracket, and assembling said first and second enclosure components so as to form said housing, said mounting aperture of said housing is situated around said sidewall of said substrate coupling, and said substrate coupling mounting area and said mounting bracket is enclosed by said housing, while said module component access apertures formed in said housing engage one or more of said mounted modular components so as to provide exterior access to portions of said mounted modular components, while retaining said housing in place.

15. The apparatus of claim 14, wherein said housing is formed to allow portions of said modular components to be accessible exterior said housing to access and monitor same.

16. The apparatus of claim 15, wherein said modular components comprise modular sample components configured to condition pressurized fluid from said extraction device, providing conditioned fluid.

17. The apparatus of claim 16, wherein said conditioned fluid comprises a gas.

18. The apparatus of claim 17, wherein said housing is insulated, and a heater for selectively heating fluid passing through said modular components.

19. The apparatus of claim 16, wherein said module mounting area of said mounting bracket has module component mounting apertures formed along its length to receive said modular components, and said enclosure components are formed to engage along their length to form said housing, said housing having formed there along module component access apertures aligned with said module component mounting apertures of said module mounting area, so as to allow the passage of portions of said mounted modular components through said housing, so as to provide access to said modular components exterior to said housing.

20. The apparatus of claim 19, wherein said mounted modular components exterior to said housing to are positioned facilitate exterior access to same as well as condition fluid flowing therethrough, while engaging said housing to support and retain said housing in place.

21. The apparatus claim 15, wherein said first and second enclosure components enclose said module mounting area of said substrate bracket, forming a housing, while allowing the passage of portions of said mounted modular components for access exterior said housing.

22. The apparatus of claim 21, wherein said housing is formed to allow the passage of said extraction device through said substrate coupling without the need to remove said mounting bracket or said substrate coupling, as well as allow each enclosure module to be removed independently without hinges.

23. The apparatus of claim 21, wherein said fluid extraction device is a sample probe.

24. The apparatus of claim 21, wherein said enclosure components are secured to one another via pins to selectively form said housing.

25. The apparatus of claim 21, wherein said enclosure components are secured to one another via clips to selectively form said housing.

26. The apparatus of claim 14, wherein said enclosure components are formed to engage one another while interfacing with said mounted modular components and substrate coupling so as to provide a structural integration therebetween, said integration enhancing stability, while increasing rigidity of the system and retaining said housing in place.

27. The apparatus of claim 14 wherein said substrate coupling further comprises a substrate coupling base orthogonally emanating from said sidewall in the vicinity of said first end of said substrate coupling;
whereby, upon positioning said first and second enclosure components about said substrate coupling and substrate bracket, and assembling said first and second enclosure components so as to form said housing, said mounting aperture of said housing is situated around said sidewall of said substrate coupling, with said housing situated above said substrate coupling base.

28. The apparatus of claim 27, wherein said substrate coupling base comprises a hexagonal configuration.

* * * * *